(12) United States Patent
Zhang et al.

(10) Patent No.: US 10,364,149 B2
(45) Date of Patent: Jul. 30, 2019

(54) HYDROGEN GENERATION SYSTEM AND FUEL CELL SYSTEM

(71) Applicant: Panasonic Intellectual Property Management Co., Ltd., Osaka (JP)

(72) Inventors: Jin Zhang, Osaka (JP); Shigenori Onuma, Kyoto (JP); Hidenobu Wakita, Kyoto (JP); Yoichiro Tsuji, Osaka (JP); Akinori Yukimasa, Nara (JP); Hiromi Kita, Nara (JP); Masashi Morita, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 159 days.

(21) Appl. No.: 15/721,961

(22) Filed: Oct. 2, 2017

(65) Prior Publication Data

US 2018/0105418 A1  Apr. 19, 2018

(30) Foreign Application Priority Data

Oct. 13, 2016  (JP) .................... 2016-201795

(51) Int. Cl.
*C01B 3/24* (2006.01)
*C01B 3/38* (2006.01)
(Continued)

(52) U.S. Cl.
CPC .............. *C01B 3/24* (2013.01); *C01B 3/38* (2013.01); *C07C 5/373* (2013.01); *H01M 8/0618* (2013.01); *H01M 8/22* (2013.01); *C01B 2203/0233* (2013.01); *C01B 2203/0244* (2013.01); *C01B 2203/066* (2013.01);
(Continued)

(58) Field of Classification Search
CPC ........... H01M 8/0618; C01B 3/24; C01B 3/38
See application file for complete search history.

(56) References Cited

U.S. PATENT DOCUMENTS

| | | | | |
|---|---|---|---|---|
| 2005/0048338 A1* | 3/2005 | Kobayashi | ........ | H01M 8/04007 429/414 |
| 2011/0212375 A1* | 9/2011 | Taguchi | .................... | C01B 3/38 429/425 |
| 2012/0040260 A1* | 2/2012 | Morita | .............. | H01M 8/04029 429/414 |

FOREIGN PATENT DOCUMENTS

| | | |
|---|---|---|
| JP | 2011-216208 | 10/2011 |
| JP | 2016-066534 | 4/2016 |

* cited by examiner

*Primary Examiner* — Jonathan G Jelsma
(74) *Attorney, Agent, or Firm* — McDermott Will & Emery LLP

(57) ABSTRACT

A hydrogen generation system including: a reformer generating hydrogen-containing gas using a raw material and reforming water; a combustor combusting hydrogen-containing gas and air and generating exhaust gas; a first channel passing cooling water; a condenser generating condensed water by heat exchange between exhaust gas and cooling water; a tank storing condensed water as cooling water; a pump supplying cooling water from the tank to the condenser; a second channel branching at a branch between the pump and condenser in the first channel, and passing some cooling water to the reformer as reforming water; a heater provided downstream of the branch, and heating the first channel; a temperature detector detecting the temperature of the first channel; and a controller, in an activation operation mode, determining whether the second channel is filled with reforming water, based on the temperature detected by the temperature detector after the heater has operated.

13 Claims, 12 Drawing Sheets

(51) Int. Cl.
*H01M 8/0612* (2016.01)
*C07C 5/373* (2006.01)
*H01M 8/22* (2006.01)

(52) U.S. Cl.
CPC .......... *C01B 2203/0816* (2013.01); *C01B 2203/0822* (2013.01); *C01B 2203/0827* (2013.01); *C01B 2203/1241* (2013.01); *C01B 2203/1247* (2013.01); *C01B 2203/1258* (2013.01); *C01B 2203/1604* (2013.01); *C01B 2203/169* (2013.01); *C01B 2203/1695* (2013.01); *C10J 2300/0976* (2013.01); *C10J 2300/1853* (2013.01); *Y02P 20/128* (2015.11)

HYDROGEN GENERATION SYSTEM AND FUEL CELL SYSTEM

BACKGROUND

1. Technical Field

The present disclosure relates to a hydrogen generation system which generates a hydrogen-containing gas using a raw material and reforming water, and to a fuel cell system in which the hydrogen generation system is used.

2. Description of the Related Art

There are known hydrogen generation systems which are provided with: a reformer which generates a hydrogen-containing gas from a raw material, such as natural gas or LPG, and vaporized reforming water; a vaporizer which vaporizes the reforming water; a raw material supplier which supplies the raw material to the reformer; a reforming water supply means which supplies the reforming water to the vaporizer; and a water tank which accumulates the reforming water.

In such hydrogen generation systems, if there is a shortage in the supply of reforming water, the reaction equilibrium breaks down in the reformer, thereby causing carbonization of the raw material to occur on the catalyst, degradation of the reform catalyst to occur, and giving rise to a decline in the capability to generate the hydrogen-containing gas. Thus, systems provided with a configuration for detecting this shortage in the supply of reforming water have been proposed (for example, Japanese Unexamined Patent Application Publication Nos. 2011-216208 and 2016-66534).

In a fuel cell system according to Japanese Unexamined Patent Application Publication No. 2011-216208, a temperature detection means which detects the temperature of a vaporizer is provided, the amount of reforming water supplied is increased if the temperature detected by the temperature detection means becomes equal to or greater than a predetermined temperature, and a water supply abnormality is determined in the case where the rise in the temperature detected by the temperature detection means continues.

Furthermore, in a fuel cell system according to Japanese Unexamined Patent Application Publication No. 2016-66534, a control device determines that reforming water has been supplied up to a predetermined water level of a reforming water supply pipe, based on changes in the temperature detected by a temperature sensor arranged between a reforming water supply pump for the reforming water supply pipe and an evaporation unit.

SUMMARY

One non-limiting and exemplary embodiment provides a hydrogen generation system which is inexpensive and capable of detecting a shortage in the supply of reforming water with high reliability without causing a decline in the performance of a reformer.

In one general aspect, the techniques disclosed here feature a hydrogen generation system provided with: a reformer which generates a hydrogen-containing gas using a raw material and reforming water; a combustor which combusts the hydrogen-containing gas generated by the reformer and air to generate an exhaust gas; an exhaust gas channel through which the exhaust gas is made to flow; a cooling water channel through which cooling water is made to flow in order to cool the exhaust gas; a condenser which causes moisture within the exhaust gas to be condensed by heat exchange between the exhaust gas and the cooling water to generate condensed water; a water tank which accumulates, as the cooling water, the condensed water generated in the condenser; a water supply pump which causes the cooling water accumulated inside the water tank to be supplied to the condenser; a reforming water channel which branches at a first branching part provided between the water supply pump and the condenser in the cooling water channel, and through which a portion of the cooling water is made to flow to the reformer as the reforming water; a heater which is provided further downstream than the first branching part in a flow direction of the cooling water in the cooling water channel, and which heats the cooling water channel; a first temperature detector which detects the temperature of the cooling water channel heated by the heater; and a controller, in which, in an activation operation mode which is an operation mode from activation to steady operation of the hydrogen generation system, the controller causes the heater to operate, and determines whether or not the inside of the reforming water channel is filled with the reforming water, based on the temperature detected by the first temperature detector after the heater has operated.

The aspect of the present disclosure demonstrates the effect of being inexpensive and capable of detecting a shortage in the supply of reforming water with high reliability without causing a decline in the performance of the reformer.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

Figure 1:
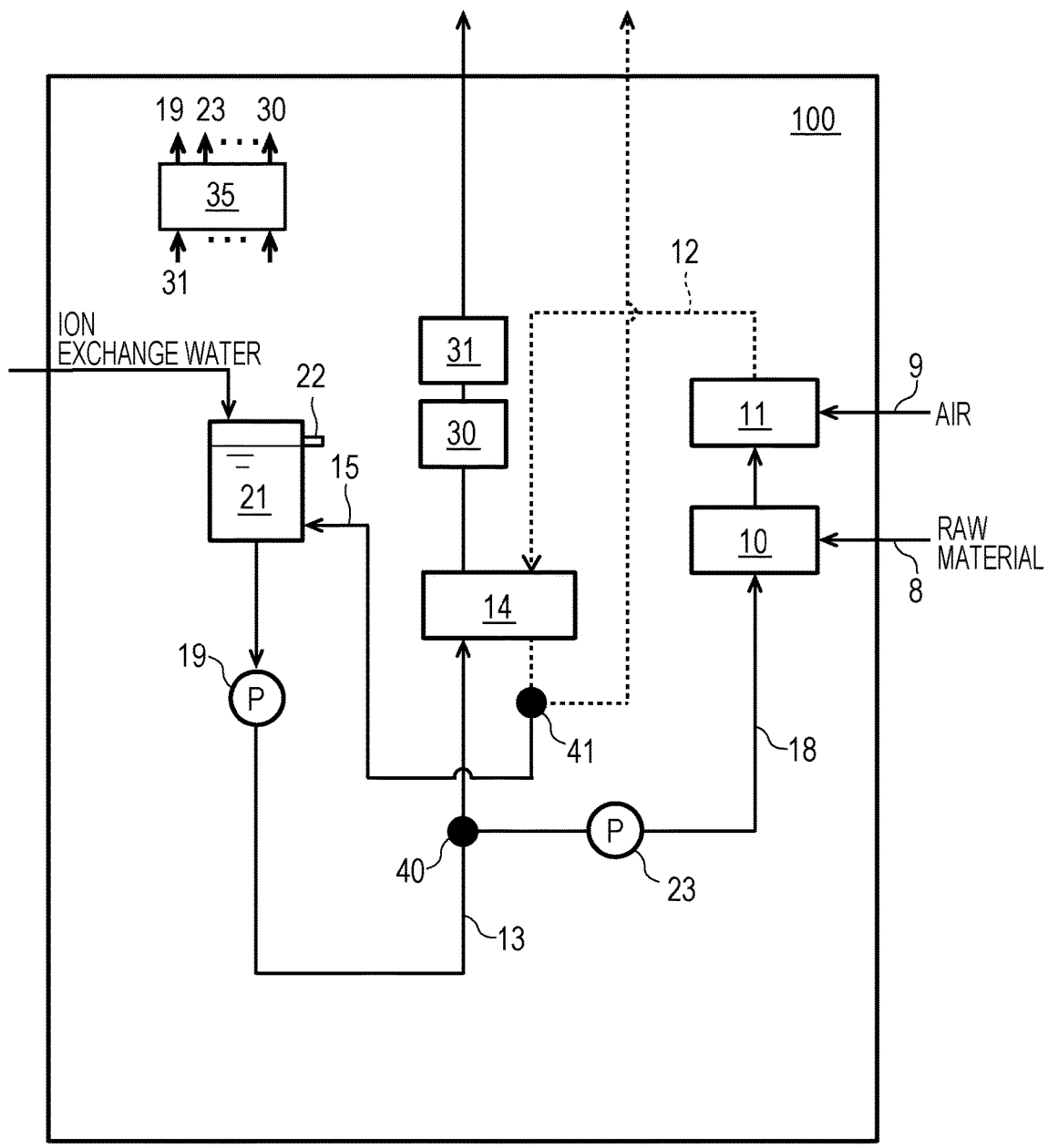
FIG. 1 is a drawing depicting an example of a schematic configuration of a hydrogen generation system according to embodiment 1 of the present disclosure.

DETAILED DESCRIPTION (Underlying Knowledge Forming Basis of the Present Disclosure)

The present inventors carried out a diligent investigation with respect to Japanese Unexamined Patent Application Publication Nos. 2011-216208 and 2016-66534 as prior hydrogen generation systems. As a result, the following findings were obtained. It should be noted that, in the present specification, a hydrogen generation system being in a stopped/standby state is referred to as a stopped/standby mode, and a state in which a predetermined amount of hydrogen-containing gas is being stably generated in a reformer 10, which is described later on, is referred to as a steady operation mode. Furthermore, a state in which the devices provided in the hydrogen generation system are sequentially made to operate from the stopped/standby mode to the steady operation mode being reached is referred to as an activation operation mode. Moreover, it is assumed that the activation operation mode also includes abnormality detection processing, which is described later on.

The fuel cell system disclosed in Japanese Unexamined Patent Application Publication No. 2011-216208 has a configuration in which a control means increases the output of a water supply means if the temperature detected by a temperature detection means provided inside a vaporizer becomes equal to or greater than a predetermined temperature, for example. That is, the fuel cell system disclosed in Japanese Unexamined Patent Application Publication No. 2011-216208 has a configuration in which a subject (temperature determination site) at which the temperature is to be detected by a temperature detection unit is inside a vaporizer, and it is possible to determine that the temperature inside the vaporizer has risen due to a shortage of reforming water if the detected temperature becomes equal to or greater than a predetermined temperature. With a configuration such as this, it was noticed that, at the point in time when it is determined that the temperature detected by the temperature detection means has become equal to or greater than the predetermined temperature, a shortage of reforming water has already occurred, and the performance of the reformer may have declined. Furthermore, in the fuel cell system disclosed in Japanese Unexamined Patent Application Publication No. 2011-216208, in the case where the reforming water supply pump is malfunctioning in the activation operation mode or the case where there has been an abnormality in a supply channel or the like which supplies reforming water to the vaporizer, there is a risk of continuing to execute the activation operation mode without noticing these defects and of reforming water of the predetermined amount not being supplied to the vaporizer.

The fuel cell system disclosed in Japanese Unexamined Patent Application Publication No. 2016-66534 has a configuration in which a temperature sensor is arranged in a reforming water supply pipe, and, during the activation operation mode, a control device is able to determine that reforming water has been supplied up to a predetermined water level, based on changes in the temperature detected by this temperature sensor. It therefore becomes possible for an abnormality in the supply of reforming water to the reformer to be determined during the activation operation mode disclosed in Japanese Unexamined Patent Application Publication No. 2016-66534. Incidentally, the fuel cell system disclosed in Japanese Unexamined Patent Application Publication No. 2016-66534 has a configuration in which an exhaust gas is condensed in order to obtain the reforming water. Furthermore, stored hot water is used as a heating medium for causing the exhaust gas to condense. Therefore, in order to obtain reforming water in a stable manner, a detection means is required to confirm that stored hot water of a predetermined flow rate is flowing inside a stored hot water circulation line provided separately from the reforming water supply pipe, which incurs costs. Furthermore, in the case where tap water is used for the stored hot water, the tap water includes metal ions such as calcium and magnesium, and therefore, when the tap water is heated by heat exchange with the exhaust gas, there is a possibility that metal oxides (scale) may be produced from the metal ions. In the case where this scale accumulates inside a heat exchanger or inside the stored hot water circulation line, problems occur such as the heat exchange efficiency declining and the heat exchanger and piping becoming clogged and it becoming difficult for the stored hot water to flow. To deal with these problems, for example, it is feasible for the stored hot water circulation line to be formed of piping to which it is difficult for scale to adhere; however, a configuration such as this leads to an increase in the cost of the system.

Thus, the present inventors carried out a diligent investigation with respect to a hydrogen generation system which is inexpensive and capable of detecting a shortage in the supply of reforming water without causing degradation of a reform catalyst. Then, in a hydrogen generation system in which cooling water is supplied as a heating medium to a condenser that generates condensed water from an exhaust gas that includes moisture, when adopting a configuration in which a portion of the cooling water can be supplied to a vaporizer as reforming water before reaching the condenser, it was noticed that, by determining that there is a shortage in the supply of the cooling water, it is consequently possible to also determine that there is a shortage in the supply of the reforming water. More specifically, it was noticed that a detection mechanism which is described later on can be provided at a location in a cooling water channel that is further downstream than a first branching part, which is a section where a reforming water channel through which reforming water flows branches from a cooling water channel through which cooling water flows, and a determination as to whether or not reforming water is to be supplied can be carried out based on a determination by the detection mechanism as to whether or not cooling water is to be supplied.

Based on the above findings, the present inventors discovered that it is possible to realize a hydrogen generation system which is inexpensive and capable of detecting a shortage in the supply of reforming water without causing a decline in the performance of the reformer, and a fuel cell system in which the hydrogen generation system is used, and arrived at the present disclosure. Also, in the present disclosure, specifically, the aspects given hereinafter are provided.

In order to solve the aforementioned problems, a hydrogen generation system according to a first aspect of the present disclosure is provided with: a reformer which generates a hydrogen-containing gas using a raw material and reforming water; a combustor which combusts the hydrogen-containing gas generated by the reformer and air to generate an exhaust gas; an exhaust gas channel through which the exhaust gas is made to flow; a cooling water channel through which cooling water is made to flow in order to cool the exhaust gas; a condenser which causes moisture within the exhaust gas to be condensed by heat exchange between the exhaust gas and the cooling water to generate condensed water; a water tank which accumulates, as the cooling water, the condensed water generated in the condenser; a water supply pump which causes the cooling water accumulated inside the water tank to be supplied to the condenser; a reforming water channel which branches at a first branching part provided between the water supply pump and the condenser in the cooling water channel, and through which a portion of the cooling water is made to flow to the reformer as the reforming water; a heater which is provided further downstream than the first branching part in the flow direction of the cooling water in the cooling water channel, and which heats the cooling water channel; a first temperature detector which detects the temperature of the cooling water channel heated by the heater; and a controller, in which, in an activation operation mode which is an operation mode from activation to steady operation of the hydrogen generation system, the controller causes the heater to operate, and determines whether or not the inside of the reforming water channel is filled with the reforming water, based on the temperature detected by the first temperature detector after the heater has operated.

According to the aforementioned configuration, because the first temperature detector is provided, it is possible to comprehend temperature changes which accompany the heating performed by the heater in the cooling water channel in the activation operation mode. That is, the way in which the temperature of the cooling water channel changes is different in the case where the cooling water channel is filled with cooling water and in the case where the cooling water channel is not filled with cooling water. For that reason, the controller is able to determine whether or not the cooling water channel is filled with cooling water, based on the temperature detected by the first temperature detector.

Furthermore, due to adopting a configuration which is provided with the cooling water channel through which cooling water is made to flow and the reforming water channel which branches at the first branching part in the cooling water channel and through which a portion of the cooling water is made to flow to the reformer as reforming water, by determining whether or not the cooling water channel is filled with cooling water, it is consequently possible to determine whether or not the reforming water channel is filled with reforming water.

It is therefore possible to suppress manufacturing costs compared to a configuration in which, for example, the cooling water channel and the reforming water channel are configured in such a way as to be channels of separate systems, and whether or not the respective channels are filled with cooling water or reforming water is detected separately.

Thus, the hydrogen generation system according to the first aspect of the present disclosure demonstrates the effect of being inexpensive and capable of detecting a shortage in the supply of reforming water with high reliability without causing a decline in the performance of the reformer.

A hydrogen generation system according to a second aspect of the present disclosure may have a configuration in which, in the aforementioned first aspect, the controller performs control in such a way that operation in the activation operation mode is made to stop when it is determined that the inside of the reforming water channel is not filled with the reforming water.

According to the aforementioned configuration, a configuration is adopted in which the controller performs control in such a way that operation in the activation operation mode is made to stop when it is determined that the inside of the reforming water channel is not filled with the reforming water, and therefore the operation of the hydrogen generation system in the activation operation mode can be made to stop without causing a decline in the performance of the reformer.

A hydrogen generation system according to a third aspect of the present disclosure may have a configuration in which, in the aforementioned first aspect, in the activation operation mode, the controller performs control in such a way that the heater is made to operate before the combustor is made to ignite.

For a hydrogen generation system according to a fourth aspect of the present disclosure, in any one aspect of the aforementioned first to third aspects, the heater and the first temperature detector may be provided in locations which are, in the flow direction of the cooling water in the cooling water channel, further downstream than the first branching part, and higher than the first branching part.

According to the aforementioned configurations, the first temperature detector and the heater are provided in locations which are further downstream and higher than the first branching part in the cooling water channel, and it is therefore possible to guarantee that there is always reforming water inside the reforming water channel when the controller has determined that the inside of the cooling water channel is filled with cooling water, based on the temperature of the cooling water channel detected by the first temperature detector.

Therefore, the hydrogen generation system according to the fourth aspect of the present disclosure is able to accurately determine whether or not there is reforming water.

For a hydrogen generation system according to a fifth aspect of the present disclosure, in any one aspect of the aforementioned first to third aspects, the cooling water channel may be a circulation channel in which the cooling water circulates flowing through the water tank, the water supply pump, the first branching part, the condenser, the heater, and the first temperature detector.

According to the aforementioned configuration, the cooling water channel is a circulation channel, and it is therefore not necessary for cooling water to be supplied to the water tank from outside. Thus, the hydrogen generation system according to the fifth aspect of the present disclosure can be a self-contained system in which cooling water flowing through the cooling water channel and condensed water generated by the condenser can be used as cooling water and condensed water.

For a hydrogen generation system according to a sixth aspect of the present disclosure, in the aforementioned fifth aspect, the heater and the first temperature detector may be provided in locations which are higher than the first branching part, and in a section between the condenser and the water tank in the cooling water channel.

According to the aforementioned configuration, the first temperature detector and the heater are provided locations which are higher than the first branching part and in a section between the condenser and the water tank in the cooling water channel, and it is therefore possible to guarantee that there is always reforming water inside the reforming water channel when the controller has determined that the inside of the cooling water channel is filled with cooling water, based on the temperature of the cooling water channel detected by the first temperature detector.

Therefore, the hydrogen generation system according to the sixth aspect of the present disclosure is able to accurately determine whether or not there is reforming water.

A hydrogen generation system according to a seventh aspect of the present disclosure may have a configuration in which, in any one aspect of the aforementioned first to sixth aspects, in a steady operation mode which is an operation mode in which the hydrogen generation system is in steady operation, the first temperature detector detects the temperature of the cooling water which is discharged from the condenser, and the controller determines whether or not there is an abnormality in the hydrogen generation system in the steady operation mode, based on the temperature detected by the first temperature detector.

According to the aforementioned configuration, the controller is able to comprehend the temperature of the cooling water discharged from the condenser, in the steady operation mode, from the detection result obtained by the first temperature detector. Therefore, the hydrogen generation system according to the seventh aspect of the present disclosure is able, by the controller, to determine whether or not there is an abnormality in the hydrogen generation system in the steady operation mode, such as whether or not the combustor is operating normally, for example.

For a hydrogen generation system according to an eighth aspect of the present disclosure, in any one aspect of the aforementioned first to seventh aspects, the condenser, the heater, and the first temperature detector may be arranged in this order, in the flow direction of the cooling water, in the cooling water channel.

A hydrogen generation system according to a ninth aspect of the present disclosure may have a configuration in which, in the aforementioned eighth aspect, a second temperature detector which detects the temperature of the cooling water channel is provided at a location which is further downstream than the condenser and further upstream than the heater, in the flow direction of the cooling water, in the cooling water channel, and the controller, based on the temperature detected by the second temperature detector in addition to the temperature detected by the first temperature detector, obtains the difference between the temperature detected by the first temperature detector and the temperature detected by the second temperature detector, and determines whether or not the inside of the reforming water channel is filled with the reforming water, according to this difference between the temperatures.

Here, in the case where the inside of the cooling water channel is filled with cooling water and the case where there is no cooling water inside the cooling water channel, there is a difference in the magnitude of the difference between the temperature detected by the first temperature detector and the temperature detected by the second temperature detector. For that reason, the controller is able to determine whether or not the cooling water channel is filled with cooling water, based on the difference between the temperature detected by the first temperature detector and the temperature detected by the second temperature detector.

Furthermore, due to adopting a configuration which is provided with the cooling water channel through which cooling water is made to flow and the reforming water channel which branches at the first branching part in the cooling water channel and through which a portion of the cooling water is made to flow to the reformer as reforming water, by determining whether or not the cooling water channel is filled with cooling water, it is consequently possible to determine whether or not the reforming water channel is filled with reforming water.

It is therefore possible to suppress manufacturing costs compared to a configuration in which, for example, the cooling water channel and the reforming water channel are configured in such a way as to be channels of separate systems, and whether or not the respective channels are filled with cooling water or reforming water is detected separately.

Thus, the hydrogen generation system according to the ninth aspect of the present disclosure is inexpensive and capable of detecting a shortage in the supply of reforming water with high reliability without causing a decline in the performance of the reformer.

A hydrogen generation system according to a tenth aspect of the present disclosure may have a configuration in which, in any one aspect of the aforementioned first to eighth aspects, a jig for arranging the heater in the cooling water channel is provided, and the first temperature detector is arranged in the cooling water channel as a single unit together with the heater by the jig.

A hydrogen generation system according to an eleventh aspect of the present disclosure may have a configuration in which, in any one aspect of the aforementioned first to eighth aspects, a jig for arranging the heater in the cooling water channel is provided, and the first temperature detector is arranged near the jig in the cooling water channel.

In order to solve the aforementioned problems, a fuel cell system according to a twelfth aspect of the present disclosure is provided with: a reformer which generates a hydrogen-containing gas using a raw material and reforming water; a fuel cell which generates electricity using the hydrogen-containing gas and air; a combustor which combusts the hydrogen-containing gas and air which have not been used in generation of electricity by the fuel cell to generate an exhaust gas; an exhaust gas channel through which the exhaust gas is made to flow; a cooling water channel through which cooling water is made to flow in order to cool the exhaust gas; a condenser which causes moisture within the exhaust gas to be condensed by heat exchange between the exhaust gas and the cooling water to generate condensed water; a water tank which accumulates, as the cooling water, the condensed water generated in the condenser; a water supply pump which causes the cooling water accumulated inside the water tank to be supplied to the condenser; a reforming water channel which branches at a first branching part provided between the water supply pump and the condenser in the cooling water channel, and through which a portion of the cooling water is made to flow to the reformer as the reforming water; a heater which is provided further downstream than the first branching part in the flow direction of the cooling water in the cooling water channel; a first temperature detector which detects the temperature of the cooling water channel heated by the heater; and a controller, in which, in an activation operation mode which is an operation mode from activation to steady operation of the fuel cell system, the controller causes the heater to operate, and determines whether or not the inside of the reforming water channel is filled with the reforming water, based on the temperature detected by the first temperature detector after the heater has operated.

According to the aforementioned configuration, because the first temperature detector is provided, it is possible to comprehend temperature changes which accompany the heating performed by the heater in the cooling water channel in the activation operation mode. That is, the way in which the temperature of the cooling water channel changes is different in the case where the cooling water channel is filled with cooling water and in the case where the cooling water channel is not filled with cooling water. For that reason, the controller is able to determine whether or not the cooling water channel is filled with cooling water, based on the temperature detected by the first temperature detector.

Furthermore, due to adopting a configuration which is provided with the cooling water channel through which cooling water is made to flow and the reforming water channel which branches at the first branching part in the cooling water channel and through which a portion of the cooling water is made to flow to the reformer as reforming water, by determining whether or not the cooling water channel is filled with cooling water, it is consequently possible to determine whether or not the reforming water channel is filled with reforming water.

It is therefore possible to suppress manufacturing costs compared to a configuration in which, for example, the cooling water channel and the reforming water channel are configured in such a way as to be channels of separate systems, and whether or not the respective channels are filled with cooling water or reforming water is detected separately.

Thus, the fuel cell system according to the twelfth aspect of the present disclosure demonstrates the effect of being inexpensive and capable of detecting a shortage in the supply of reforming water with high reliability without causing a decline in the performance of the reformer.

For a fuel cell system according to a thirteenth aspect of the present disclosure, in the aforementioned twelfth aspect, the fuel cell may be a solid oxide fuel cell.

Hereinafter, embodiment 1 of the present disclosure will be described with reference to the drawings. It should be noted that, hereinafter, the same or corresponding constituent members are denoted by the same reference numbers throughout all of the drawings, and there are cases where descriptions thereof are omitted.

Embodiment 1

(Configuration of Hydrogen Generation System)

The configuration of a hydrogen generation system 100 according to embodiment 1 of the present disclosure will be described with reference to FIG. 1. FIG. 1 is a drawing depicting an example of a schematic configuration of the hydrogen generation system 100 according to embodiment 1 of the present disclosure. The hydrogen generation system 100 is a system which generates a hydrogen-containing gas using a raw material supplied from outside and reforming water (ion exchange water).

As depicted in FIG. 1, the hydrogen generation system 100 has a configuration which is provided with a raw material supply channel 8, an air supply channel 9, a reformer 10, a combustor 11, an exhaust gas channel 12, a cooling water channel 13, a condenser 14, a condensed water channel 15, a reforming water channel 18, a water supply pump 19, a water tank 21, a reforming water supply pump 23, a heater 30, a first temperature detector 31, and a controller 35. The heater 30 and the first temperature detector 31 constitute a detection mechanism which detects whether or not there is cooling water in the cooling water channel 13, in other words, whether or not there is reforming water in the reforming water channel 18. It should be noted that, in the present specification, a state in which the inside of the cooling water channel 13 is filled with cooling water is taken as a state in which there is cooling water, and a state in which the reforming water channel 18 is filled with reforming water is taken as a state in which there is reforming water.

Furthermore, in the hydrogen generation system 100, a state in which the operation of devices such as the combustor 11, the water supply pump 19, the reforming water supply pump 23, and the heater 30 is stopped and hydrogen is not generated is referred to as a stopped/standby mode. Furthermore, a state in which the aforementioned devices are made to operate and hydrogen is generated is referred to as a steady operation mode. Furthermore, a state in which the aforementioned devices are sequentially made to operate from the stopped/standby mode to the steady operation mode being reached is referred to as an activation operation mode. It is assumed that the activation operation mode also includes abnormality detection processing, which is described later on.

The reformer 10 is a reactor which generates a hydrogen-containing gas using a raw material and reforming water. Specifically, in the reformer 10, a hydrogen-containing gas is generated by a reforming reaction using the raw material and steam (reforming water) in the presence of a reform catalyst. A possible example of the reforming reaction carried out in the reformer 10 is a steam reforming reaction or an autothermal reaction.

Although not particularly depicted in FIG. 1, the hydrogen generation system 100 is appropriately provided with the devices required for the reforming reaction. For example, in the case where a steam reforming reaction is to be carried out in the reformer 10, an evaporator which generates steam from reforming water is provided. It should be noted that the raw material is supplied to the reformer 10 through the raw material supply channel 8 by a raw material supplier which is not depicted. The raw material supplier can be a device which makes it possible to adjust the flow rate of the raw material supplied to the reformer 10, and, for example, may be constituted by a booster and a flowmeter. A possible example of a booster is a pump or the like. A possible example of a pump is a motor-driven constant-volume pump or the like. Furthermore, a possible example of a flowmeter is a heat quantity sensor or the like.

A possible example of the raw material supplied to the reformer 10 is a gas or the like which includes organic compounds formed from at least carbon and hydrogen such as town gas in which methane is the main component, natural gas, or LPG in which propane or butane is the main component. Furthermore, a possible example of a raw material supply source is a gas cylinder, a gas infrastructure, or the like. Furthermore, there are cases where a sulfur compound is included in the raw material as an odorant or as a component derived from the raw material. In this case, a configuration can be adopted in which a desulfurizer (not depicted) is additionally provided further upstream than the reformer 10 in the raw material supply channel 8.

The combustor 11 is a device which combusts the hydrogen-containing gas generated by the reformer 10 and air supplied from outside, and a possible example is a burner. An exhaust gas is produced by the combustion of the hydrogen-containing gas and the air in the combustor 11. It should be noted that the air is supplied to the combustor 11 through the air supply channel 9 by an air supplier which is not depicted. The air supplier is a device which makes it possible to adjust the flow rate of the air supplied to the combustor 11, and may be constituted by a booster, a flowmeter, or the like. A possible example of a booster is a pump or the like. A possible example of a pump is a motor-driven constant-volume pump, an electromagnetically driven diaphragm pump, or the like. Furthermore, a possible example of a flowmeter is a heat quantity sensor or the like.

Furthermore, in the case where a steam reforming reaction is to be carried out in the reformer 10, since a steam reforming reaction is an endothermic reaction, the heat required for the reaction is provided for by the combustion heat produced by the combustor 11. Specifically, a configuration may be adopted in which the exhaust gas generated by the combustor 11 is, for example, subjected to heat exchange with the reformer 10 via the exhaust gas channel 12 which is provided in such a way as to make contact with an outer wall of the reformer 10, supplied to the condenser 14 after the reformer 10 has been heated to 650° C. for example, and then discharged outside.

The exhaust gas channel 12 is a channel through which the exhaust gas produced by the combustion of the hydrogen-containing gas and air in the combustor 11 is made to flow. In the exhaust gas channel 12, an end part which is upstream in the flow direction of the exhaust gas is connected to the combustor 11, and the exhaust gas is released into the atmosphere via an exhaust port provided in a downstream end part. The condenser 14 is provided midway along the exhaust gas channel 12.

The condenser 14 is a device that causes moisture within the exhaust gas to be condensed by heat exchange between the exhaust gas and the cooling water to generate condensed water. In other words, the aforementioned exhaust gas channel 12 and the cooling water channel 13 which is described later on are both connected to the condenser 14, and heat exchange takes place between the exhaust gas which flows through the exhaust gas channel 12 and the cooling water which flows through the cooling water channel 13. The condenser 14 then causes the exhaust gas to be cooled by heat exchange with the cooling water, causes steam included within the exhaust gas to be condensed to generate condensed water. It should be noted that it is sufficient as long as the condenser 14 has a configuration which is capable of causing the steam within the exhaust gas to condense, and a possible example is a plate-type heat exchanger. It should be noted that, since the temperature of the exhaust gas which flows through the condenser 14 becomes a high temperature (approximately 200° C., for example), the condenser 14 may be configured of a heat-resistant material such as a stainless steel, for example, SUS304, SUS316L, or SUS430.

Furthermore, in the exhaust gas channel 12, a second branching part 41 is provided at a stage subsequent to the condenser 14, and the condensed water channel 15, which branches from the exhaust gas channel 12 at the second branching part 41, is connected to the water tank 21. In other words, the condensed water channel 15 links the condenser 14 and the water tank 21, and causes the condensed water to flow from the condenser 14 toward the water tank 21. Therefore, the condensed water generated by the condenser 14 separates from the exhaust gas at the second branching part 41, flows through the condensed water channel 15, and is supplied to the water tank 21. The condensed water is accumulated in the water tank 21, and is then used as cooling water. The condensed water channel 15 may have any kind of configuration as long as condensed water is able to flow therethrough. A possible example is a resin tube of cross-linked polyethylene or the like, or a metal pipe of a stainless steel or the like, such as SUS304, SUS316L, or SUS430. Furthermore, although not depicted, in the hydrogen generation system 100, in the case where the installation location of the condenser 14 is lower than the installation location of the water tank 21, a configuration may be adopted in which a pump is provided in the condensed water channel 15, and condensed water is supplied to the water tank 21 by this pump.

The cooling water channel 13 is a channel through which condensed water is made to flow, the condensed water being used as a heating medium for causing exhaust gas to condense in the condenser 14. The water tank 21, the water supply pump 19, the condenser 14, the heater 30, and the first temperature detector 31 are arranged in this order on the cooling water channel 13 from the upstream side in the flow direction of the cooling water. In the cooling water channel 13, the cooling water accumulated in the water tank 21 by the water supply pump 19 is output and flows inside the cooling water channel 13. Then, when the condensed water flows through the condenser 14, heat exchange with the exhaust gas is carried out as mentioned above, and the temperature of the condensed water itself rises to 60 to 80° C. whereas the exhaust gas is cooled. Therefore, it is desirable that the cooling water channel 13, particularly the portion of the channel after the condenser 14, be configured of a resin tube of cross-linked polyethylene or the like, or a metal pipe of a stainless steel or the like, such as SUS304, SUS316L, or SUS430. In the embodiments of the present disclosure, the cooling water which flows through the cooling water channel 13 passes through the condenser 14 and is then discharged outside the system via the heater 30 and the first temperature detector 31.

It should be noted that the hydrogen generation system 100 according to embodiment 1 of the present disclosure has a configuration in which ion exchange water supplied to the water tank 21 from outside and condensed water supplied to the water tank 21 from the condenser 14 are used as cooling water, rather than a configuration in which tap water is used as cooling water. Furthermore, a first branching part 40 is provided at a location which is a stage subsequent to the water supply pump 19 and a stage prior to the condenser 14 in the cooling water channel 13. The reforming water channel 18 is provided between this first branching part 40 and the reformer 10.

The water tank 21 is a tank which accumulates cooling water. The water tank 21 is connected to the condensed water channel 15 as well as the cooling water channel 13, and accumulates condensed water, obtained by the condenser 14, as cooling water. It is sufficient as long as the water tank 21 has a configuration capable of accumulating condensed water, and, for example, the water tank 21 may be a tank made of a resin. A configuration may be adopted in which there is an overflow channel 22 for discharging condensed water that has become surplus inside the water tank 21, at a location higher than an outflow port (not depicted) for cooling water in the water tank 21 and the location where the condensed water channel 15 is connected.

In this way, the ion exchange water supplied from outside flows into the water tank 21 as cooling water, and also condensed water generated in the condenser 14 flows into the water tank 21 as cooling water. Also, the cooling water accumulated in the water tank 21 flows through the cooling water channel 13 and is supplied to the condenser 14, and is then discharged outside the system via the heater 30 and the first temperature detector 31. As a result of the cooling water flowing as mentioned above, the moisture in the exhaust gas can be made to condense and cooling water can be obtained. Furthermore, the condensed water obtained can be used as cooling water for cooling the exhaust gas.

It should be noted that the hydrogen generation system 100 has a configuration in which an ion exchange resin is provided between the water supply pump 19 and the first branching part 40 in the cooling water channel 13. A configuration may then be adopted in which the condensed water accumulated in the water tank 21 and used as cooling water is ion exchange water as a result of this ion exchange resin.

The water supply pump 19 is a pump which causes the cooling water accumulated inside the water tank 21 to be supplied to the condenser 14. The water supply pump 19 causes the cooling water accumulated inside the water tank 21 to be output and to flow inside the cooling water channel 13. A possible example of the water supply pump 19 is an impeller-type axial-flow pump.

The heater 30 heats the cooling water channel 13 in the activation operation mode, and is provided further downstream than the first branching part 40 in the flow direction of the cooling water in the cooling water channel 13. The heater 30 may be an electric heater in which a heating wire is wound in a spiral shape around the periphery of the cooling water channel 13, for example. The heater 30 is not restricted to an electric heater such as this, and a device capable of heating the cooling water channel 13 such as a ceramic heater is sufficient.

It should be noted that a safety measure with which a temperature fuse is installed in the heater 30 and the heater is disconnected when overheating occurs may be implemented. Alternatively, a configuration may be adopted in which the controller 35 performs control in such a way that the operation of the hydrogen generation system 100 is made to stop when the heater 30 overheats. Alternately, a configuration may be adopted in which the controller 35 performs control in such a way that an abnormality caused by overheating, a short circuit, or the like of the heater 30 is determined based on the temperature detected by the first temperature detector 31, and the operation of the hydrogen generation system 100 is made to stop.

The first temperature detector 31 is a detector which is provided in the cooling water channel 13 and detects the temperature of the cooling water channel 13. For example, the first temperature detector 31 may have a configuration in which the temperature of the pipe portion of the cooling water channel 13 to which the first temperature detector 31 is attached is detected. It is sufficient as long as the first temperature detector 31 is provided at a location at which it is possible to detect temperature changes of the cooling water channel 13 which accompany the heating performed by the heater 30, and, for example, the first temperature detector 31 may be provided at a stage subsequent to the heater 30 in the cooling water channel 13 as depicted in FIG. 1. Alternatively, the first temperature detector 31 may be provided at a stage prior to the heater 30 in the vicinity of the heater 30 in the cooling water channel 13.

Furthermore, the first temperature detector 31 is provided at a stage subsequent to the condenser 14 in the cooling water channel 13 as depicted in FIG. 1, and is able to detect the temperature of the cooling water after heat exchange with the exhaust gas discharged from the condenser 14. Therefore, in the hydrogen generation system 100, in the steady operation mode, the controller 35 is able to determine whether or not the combustor 11 and the like are operating normally, from time-sequential changes in the temperature detected by the first temperature detector 31. That is, in the case where the temperature of the cooling water detected by the first temperature detector 31 is lower than a predetermined temperature in the steady operation mode, the controller 35 assumes that an abnormality has occurred in the combustor 11 or the like, and is able to cause the operation of the hydrogen generation system 100 to stop. It should be noted that it is sufficient as long as the first temperature detector 31 has a configuration capable of detecting the temperature inside the cooling water channel 13, and, for example, the first temperature detector 31 may be a thermistor or the like.

Figure 2:
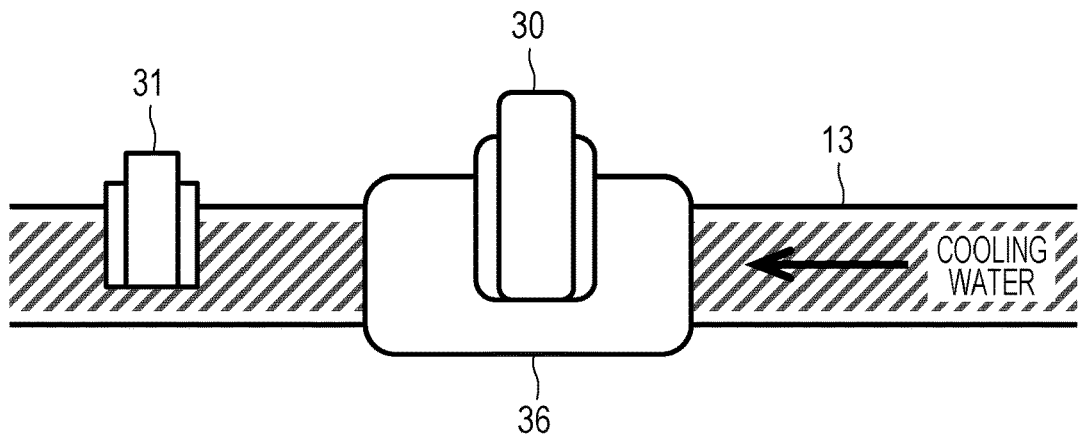
FIG. 2 is a drawing depicting an example of a configuration for attaching a heater and a first temperature detector to a cooling water channel in the hydrogen generation system depicted in FIG. 1.
Figure 3:
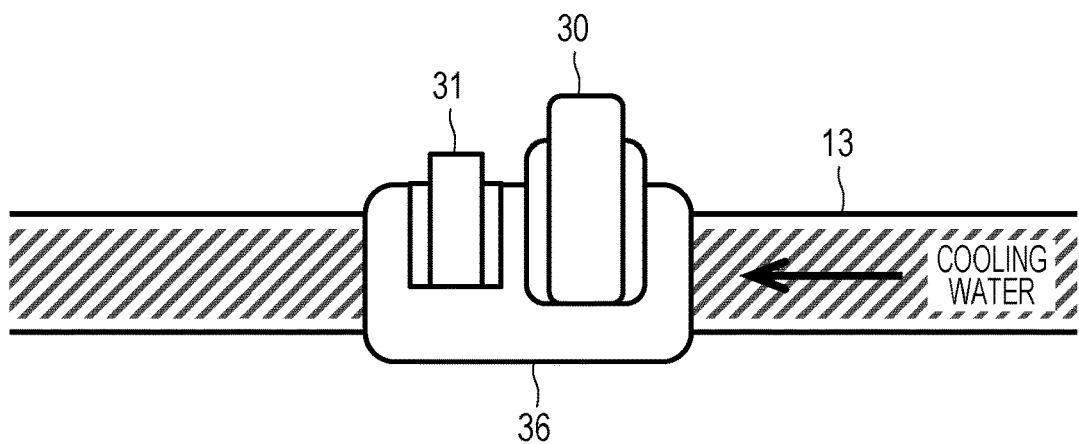
FIG. 3 is a drawing depicting an example of a configuration for attaching the heater and the first temperature detector to the cooling water channel in the hydrogen generation system depicted in FIG. 1.
Figure 4:
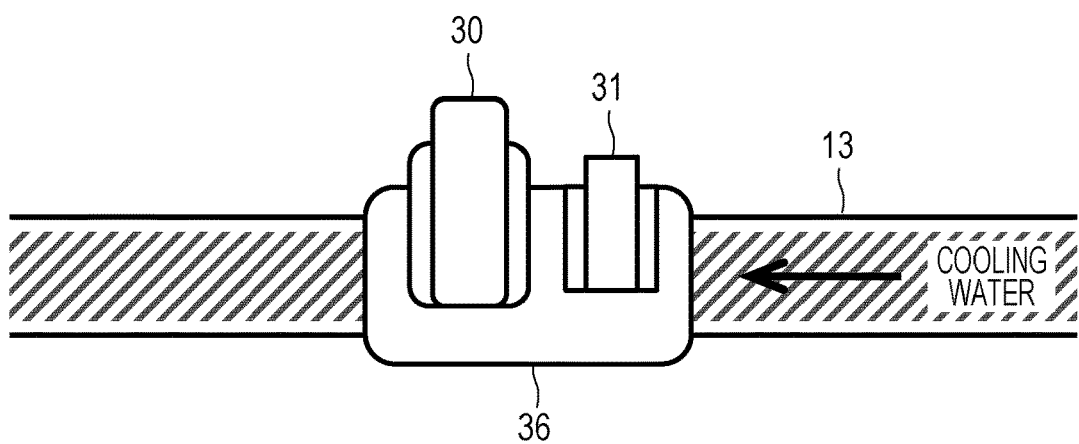
FIG. 4 is a drawing depicting an example of a configuration for attaching the heater and the first temperature detector to the cooling water channel in the hydrogen generation system depicted in FIG. 1.

The heater 30 and the first temperature detector 31 may be attached directly to the pipe of the cooling water channel 13, or may be provided on the pipe of the cooling water channel 13 by way of a jig 36 as depicted in FIGS. 2 to 4. FIGS. 2 to 4 are drawings depicting examples of configurations for attaching the heater 30 and the first temperature detector 31 to the cooling water channel 13 in the hydrogen generation system 100 depicted in FIG. 1.

In other words, as depicted in FIG. 2, a configuration may be adopted in which the heater 30 is provided by way of the jig 36 at a prior stage in the flow direction of the cooling water in the cooling water channel 13, and the first temperature detector 31 is provided directly on the pipe of the cooling water channel 13 at a stage subsequent to the heater 30. Furthermore, as depicted in FIG. 3, a configuration may be adopted in which the heater 30 is arranged at a prior stage and the first temperature detector 31 is arranged at a stage subsequent to the heater 30, and the heater 30 and the first temperature detector 31 are attached together to the cooling water channel 13 by way of the same jig 36. Alternatively, in the case where the jig 36 is configured of a material having high thermal conductivity, as depicted in FIG. 4, a configuration may be adopted in which the first temperature detector 31 is arranged at a prior stage, the heater 30 is arranged at a stage subsequent to the first temperature detector 31, and the heater 30 and the first temperature detector 31 are attached together to the cooling water channel 13 by way of the same jig 36.

It should be noted that the jig 36 is not an essential constituent element in the hydrogen generation system 100. That is, the heater 30 and the first temperature detector 31 can be attached to the cooling water channel 13 by way of the jig 36 or attached directly, according to the types of the heater 30 and the first temperature detector 31 to be attached to the pipe of the cooling water channel 13. It should be noted that the jig 36 is also deemed to be a portion of the cooling water channel 13 in the case of a configuration in which the heater 30 and the first temperature detector 31 are provided in the cooling water channel 13 by way of the jig 36.

The reforming water channel 18 is a channel which branches at the first branching part 40 provided between the water supply pump 19 and the condenser 14 in the cooling water channel 13, and causes a portion of the cooling water to flow to the reformer 10 as reforming water. It is sufficient as long as the reforming water channel 18 is a channel capable of supplying reforming water to the reformer 10, and a possible example is a resin tube of cross-linked polyethylene or the like, or a metal pipe of a stainless steel or the like, such as SUS304, SUS316L, or SUS430. It should be noted that the hydrogen generation system 100 according to embodiment 1 may have a configuration in which, as depicted in FIG. 1, a reforming water supply pump 23 such as a constant-volume cylinder pump is provided in the reforming water channel 18 in order to supply reforming water of a predetermined flow rate to the reformer 10. However, in the case of a configuration in which it is possible for reforming water of a predetermined flow rate to flow through the reforming water channel 18 from the first branching part 40 toward the reformer 10 using the pressure loss difference between the cooling water channel 13 and the reforming water channel 18, it is not always necessary for the reforming water supply pump 23 to be provided.

The controller 35 carries out various types of control for the units provided in the hydrogen generation system 100, and is provided with a computation processing unit and a storage unit which stores a control program. A possible example of the computation processing unit is an MPU, a CPU, or the like. A possible example of the storage unit is a memory or the like. The controller 35 may be constituted by an individual controller which implements centralized control, or may be constituted from a plurality of controllers which cooperate with each other to implement distributed control.

More specifically, the controller 35 performs control in such a way that, in the activation operation mode of the hydrogen generation system 100, the heater 30 is made to operate, and also the water supply pump 19 and the reforming water supply pump 23 are made to operate. Furthermore, the controller 35 is also able to perform control in such a way that the operation of the hydrogen generation system 100 is stopped based on the temperature detected by the first temperature detector 31.

Figure 5:
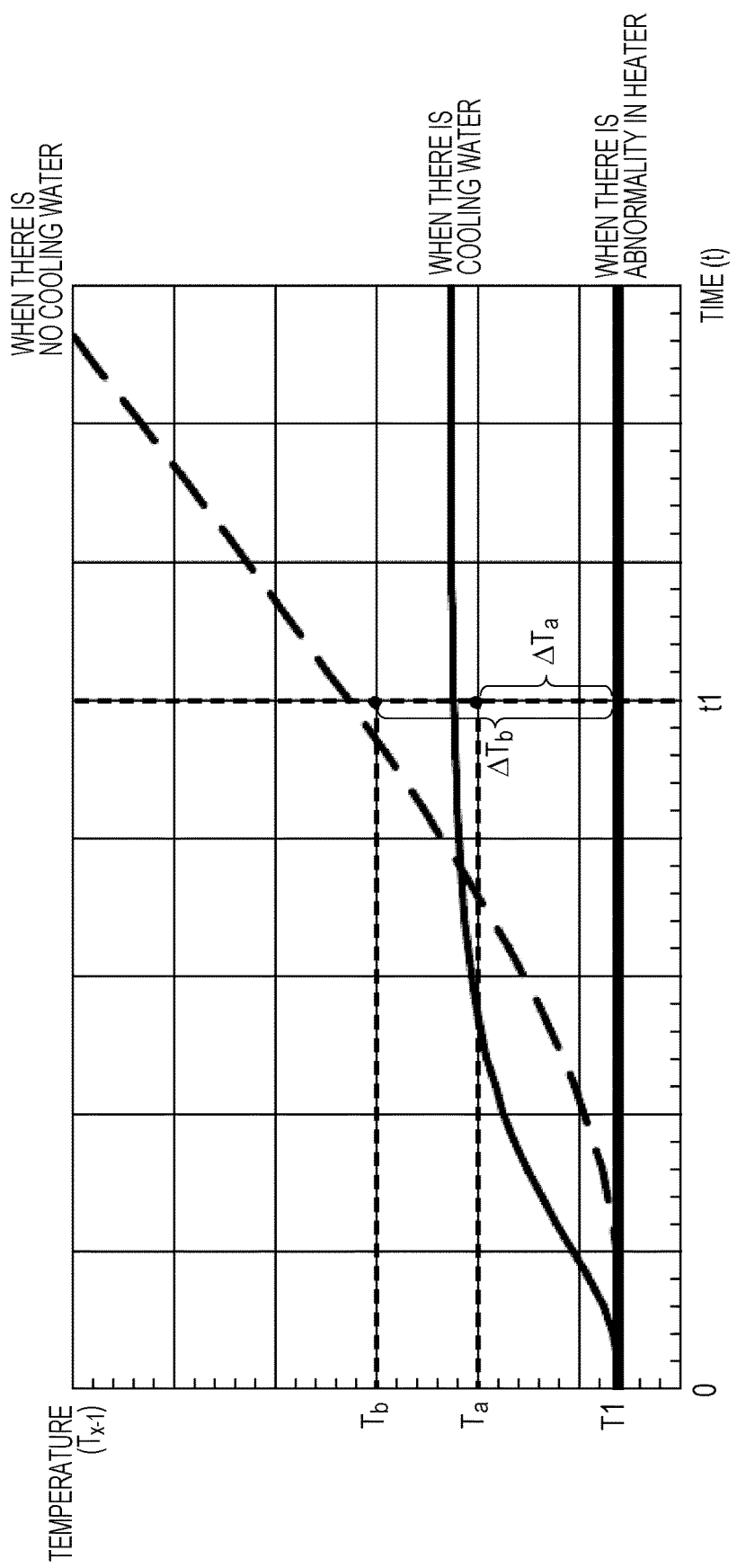
FIG. 5 is a graph depicting an example of time-sequential changes in the temperature detected by the first temperature detector provided in the hydrogen generation system depicted in FIG. 1.

In other words, at the time of commencing the activation operation mode of the hydrogen generation system 100 as depicted in FIG. 5, when the cooling water channel 13 is heated by the heater 30, the temperature detected by the first temperature detector 31 after a predetermined time (t1) is different according to whether or not there is cooling water in the cooling water channel 13. FIG. 5 is a graph depicting an example of time-sequential changes in the temperature detected by the first temperature detector 31 provided in the hydrogen generation system 100 depicted in FIG. 1. In FIG. 5, time-sequential changes in temperature are depicted for the case where the inside of the cooling water channel 13 is filled with cooling water and the case where there is no cooling water. It should be noted that the vertical axis of the graph depicted in FIG. 5 is the temperature detected by the first temperature detector 31, and the horizontal axis indicates the elapsed time from temperature detection being started by the first temperature detector 31.

As depicted in FIG. 5, in the case where there is cooling water inside the cooling water channel 13 when the activation operation mode is commenced, the temperature of the cooling water rises due to the heater 30, the temperature of the cooling water detected by the first temperature detector 31 gradually rises, and when that temperature eventually reaches a predetermined temperature, that temperature state is maintained. However, in the case where there is no cooling water inside the cooling water channel 13, the air inside the cooling water channel 13 is heated by the heater 30, and the temperature detected by the first temperature detector 31 mostly monotonically increases. It should be noted that, from the commencement of heating by the heater 30 to a fixed time such as 20 seconds, for example, the temperature becomes higher in the case where there is cooling water inside the cooling water channel 13 compared to the case where there is no cooling water, which is due to the following reason. In the case where the inside of the cooling water channel 13 is filled with water, the heat applied by the heater 30 is able to transfer to the temperature detection range of the first temperature detector 31 due to the flow of the cooling water inside the cooling water channel 13. Furthermore, the cooling water continues to flow, in an unchanged state, downstream of the first temperature detector 31. Therefore, the temperature rises in proportion to the amount of heat received, in a limited time span. That is, the amount of heat received by the water increases in a short period of time of approximately 15 to 20 seconds; however, when a long period of time of approximately one minute is reached, the temperature of the cooling water, which continues to flow, becomes a fixed value and no longer changes.

However, in the case where there is no cooling water inside the cooling water channel 13, the heat produced by the heater 30 transfers by only thermal conduction mainly through air, and transfers slowly through air which is trapped inside the cooling water channel 13 and is not flowing. Therefore, the rise in the temperature detected by the first temperature detector 31 is slow in a short period of time of approximately 15 to 20 seconds; however, when a long period of time of approximately one minute is reached, the heater 30 continues to apply heat throughout the long period of time to this trapped air, and heat is eventually transferred to the first temperature detector 31. Therefore, in a time span of approximately one minute, the temperature detected by the first temperature detector 31 becomes higher in the case where there is no cooling water inside the cooling water channel 13 compared to the case where there is cooling water inside the cooling water channel 13.

Furthermore, in the case where an abnormality has occurred in the heater 30 and the cooling water channel 13 is not heated, there are no fluctuations in the temperature detected by the first temperature detector 31, as depicted in FIG. 5.

The case where the heater 30 is installed on one surface of the pipe of the cooling water channel 13 has been described; however, in response to a temperature sensor being installed by being wound in a spiral shape about the pipe of the cooling water channel 13, the rise in the temperature detected by the first temperature detector 31 becomes quicker. Water shortage detection can be carried out effectively by optimizing of the shape, temperature measurement location, and detection timing for the heater 30 in advance by a simulation or experiment (actual device evaluation) in an appropriate manner according to the case.

The controller 35 is able to determine whether or not there is cooling water in the cooling water channel 13, based on differences in the temperature detected by the first temperature detector 31 after a predetermined time (t1) has elapsed, as mentioned above. Then, in the case where it is determined that there is no cooling water in the cooling water channel 13, the controller 35 is able to perform control in such a way that the operation of the hydrogen generation system 100 is made to stop.

Furthermore, when the temperature detected by the first temperature detector 31 becomes lower than the normal temperature in the case where the hydrogen generation system 100 is in the steady operation mode and cooling water is circulating through the cooling water channel 13, the controller 35 is also able to determine that an abnormality has occurred in the hydrogen generation system 100, such as a malfunction of the combustor 11, and perform control in such a way that the operation of the hydrogen generation system 100 is made to stop.

In this way, in the hydrogen generation system 100 according to embodiment 1, the controller 35 is configured in such a way as to be able to determine an abnormality of the hydrogen generation system 100 in the activation operation mode and the steady operation mode on the basis of the temperature detected by the first temperature detector 31.

Furthermore, in the case where the inside of the cooling water channel 13 is filled with cooling water, a state is entered in which the reforming water channel 18 which branches from the cooling water channel 13 is also filled with reforming water. Therefore, by determining whether or not there is cooling water inside the cooling water channel 13, the controller 35 is also able to determine whether or not there is reforming water inside the reforming water channel 18. Therefore, in the hydrogen generation system 100 according to embodiment 1, it is possible to detect in advance whether or not there is reforming water (cooling water) before a shortage in the supply of reforming water to the reformer 10 occurs.

(Abnormality Detection Processing in Hydrogen Generation System According to Embodiment 1)

Figure 6:
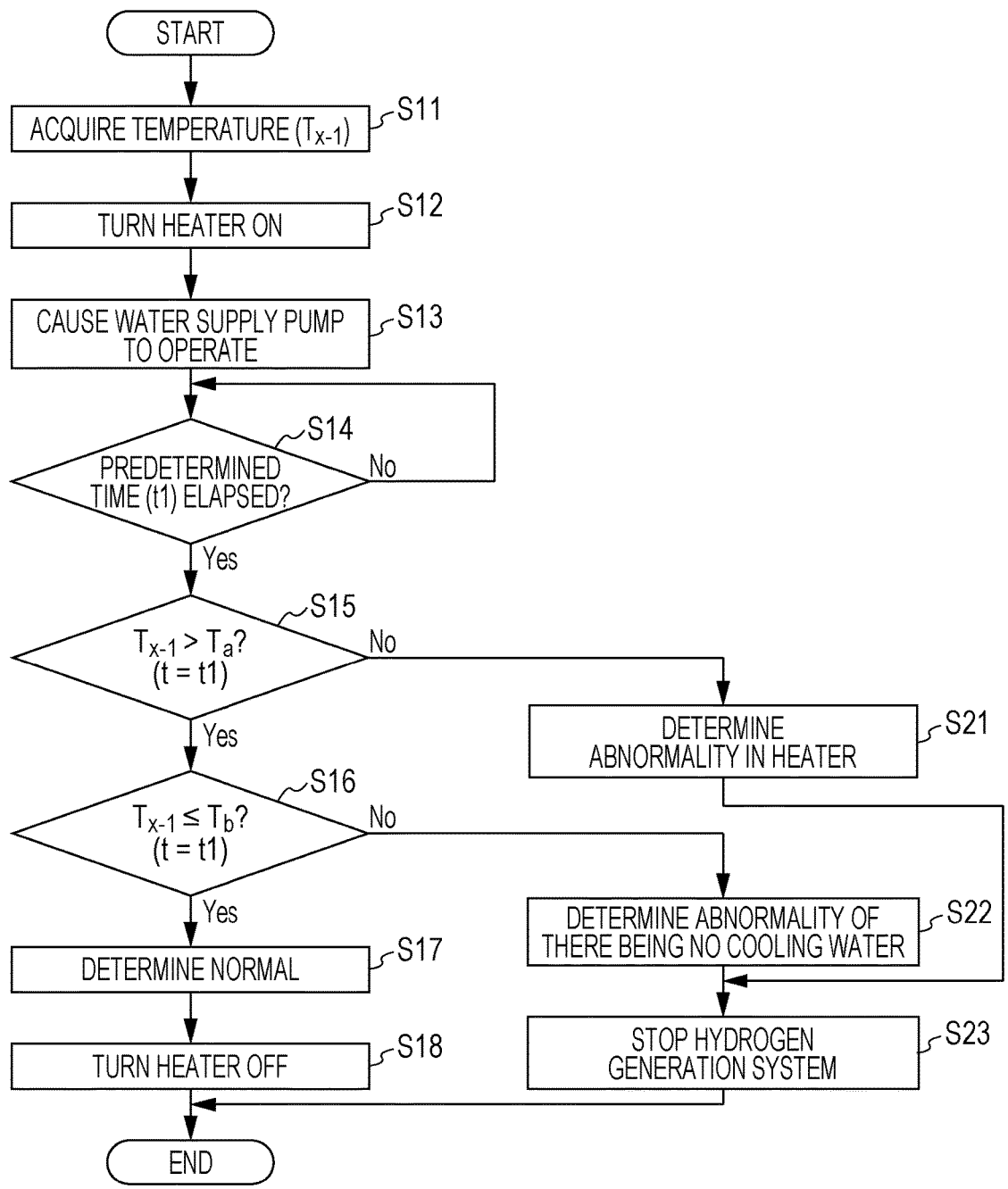
FIG. 6 is a flowchart depicting an example of abnormality detection processing in the hydrogen generation system depicted in FIG. 1.

Next, an operation flow relating to abnormality detection processing of the hydrogen generation system 100 according to embodiment 1 will be described with reference to FIG. 6 in addition to the aforementioned FIG. 5. FIG. 6 is a flowchart depicting an example of abnormality detection processing in the hydrogen generation system 100 depicted in FIG. 1. It should be noted that each processing step depicted in the flowchart of FIG. 6 is, for example, carried out by the controller 35 reading and executing a control program from a memory or the like when the activation operation mode is commenced. That is, when the operation mode of the hydrogen generation system 100 is switched from the stopped/standby mode to the activation operation mode, the controller 35 executes each step as depicted in the flowchart of FIG. 6.

First, the controller 35 acquires a temperature $T_{x-1}$ of the cooling water channel 13 detected by the first temperature detector 31 (step S11). The temperature $T_{x-1}$ acquired here is the temperature when t=0, and is therefore temperature T1. In this case, the temperature T1 is a value which fluctuates according to the environment or the like surrounding the hydrogen generation system 100, and is the room temperature, for example.

Next, the controller 35 causes current to be passed to (turns on) the heater 30, and the cooling water channel 13 is heated (step S12). Due to the heater 30 being turned on, the temperature $T_{x-1}$ of the cooling water channel 13 detected by the first temperature detector 31 rises as depicted in FIG. 5.

In addition, the controller 35 performs control in such a way that the water supply pump 19 is made to operate (step S13). Consequently, cooling water flows inside the cooling water channel 13, toward the downstream side of the cooling water channel 13.

Subsequently, the controller 35 determines whether or not a predetermined time (t1) has elapsed from the start of current being passed to the heater 30 (step S14), and continues the determination of step S14 until the predetermined time (t1) has elapsed. In the case where the predetermined time (t1) has elapsed from the start of current being passed to the heater 30 (in the case of yes in step S14), processing transitions to step S15. In step S15, it is determined whether or not the temperature $T_{x-1}$ detected by the first temperature detector 31 is higher than a temperature $T_a$ obtained by adding a predetermined temperature difference $\Delta T_a$ to the temperature T1.

It should be noted that the temperature difference $\Delta T_a$ here is a temperature by which the temperature $T_{x-1}$ is likely to at least rise when the cooling water channel 13 is heated by the heater 30 during the predetermined time (t1) in the case where cooling water has filled the inside of the cooling water channel 13, or is a temperature which is slightly lower than the aforementioned temperature, and can be obtained in advance from an actual device evaluation, simulation, or the like. This temperature difference $\Delta T_a$ is stored in a memory or the like which is not depicted. It should be noted that the predetermined time (t1) is a time in which it is possible to clearly distinguish the difference between the temperature in the case where cooling water has filled the inside of the cooling water channel 13 and the temperature in the case where there is no cooling water, and can be set as approximately 25 seconds from commencing the execution of the abnormality detection processing in the activation operation mode, for example.

Here, in the case where it is determined that the temperature $T_{x-1}$ detected by the first temperature detector 31 is equal to or less than the temperature $T_a$ (in the case of no in step S15), the controller 35 determines that the abnormality of the cooling water channel 13 not being heated due to a malfunction of the heater 30 has occurred in the hydrogen generation system 100 (step S21), and performs control in such a way that the operation of the hydrogen generation system which is in the activation operation mode is stopped (step S23).

However, in the case where it is determined that the temperature $T_{x-1}$ detected by the first temperature detector 31 is higher than the temperature $T_a$ (in the case of yes in step S15), the controller 35 transitions to step S16. Then, in step S16, the controller 35 determines whether or not the temperature $T_{x-1}$ detected by the first temperature detector 31 is equal to or less than a temperature $T_b$ obtained by adding a predetermined temperature difference $\Delta T_b$ to the temperature T1.

It should be noted that the temperature difference $\Delta T_b$ here is a temperature by which the temperature $T_{x-1}$ is likely to at least rise when the cooling water channel 13 is heated by the heater 30 during the predetermined time (t1) in the case where cooling water has not filled the inside of the cooling water channel 13, or is a temperature which is slightly lower than the aforementioned temperature, and can be obtained in advance from an actual device evaluation, simulation, or the like. The temperature difference $\Delta T_b$ is stored in a memory or the like which is not depicted.

Here, in the case where it is determined that the temperature $T_{x-1}$ detected by the first temperature detector 31 is higher than the temperature $T_b$ (in the case of no in step S16), the controller 35 determines that the abnormality of the cooling water not having filled the cooling water channel 13 has occurred (step S22), and performs control in such a way that the operation of the hydrogen generation system is stopped (step S23).

However, in the case where it is determined that the temperature $T_{x-1}$ detected by the first temperature detector 31 is equal to or less than the temperature $T_b$ (in the case of yes in step S16), the controller 35 determines that the cooling water has filled the cooling water channel 13 and that operation is normal (step S17), and transitions to step S18. In step S18, the controller 35 causes the passage of current to the heater 30 to be stopped (turned off).

Thereafter, the controller 35 causes the raw material to be supplied to the reformer 10, and causes the reforming water supply pump 23 to operate and reforming water to be supplied. Furthermore, the controller 35 causes air to be supplied to the combustor 11, and causes the combustor 11 to ignite. Then, if the temperature of the reformer 10 becomes equal to or greater than a predetermined temperature using the heat of the exhaust gas generated by the combustion in the combustor 11, the activation operation mode is ended and a transition is made to the steady operation mode.

The hydrogen generation system 100 according to embodiment 1 as mentioned above has a configuration in which a portion of the cooling water is supplied to the reformer 10 through the reforming water channel 18 which branches from the cooling water channel 13. In a configuration such as this, the heater 30 and the first temperature detector 31 are installed at a stage subsequent to the first branching part 40, and it is possible to confirm whether or not there is cooling water in the cooling water channel 13, in other words, whether or not there is reforming water in the reforming water channel 18, based on temperature changes of the cooling water channel 13 which accompany the heating performed by the heater 30 and are detected by the first temperature detector 31. In this way, with the hydrogen generation system 100 according to embodiment 1, it is possible to determine, from the state of the cooling water channel 13, a shortage in the supply of reforming water to the reformer 10 in the activation operation mode.

Furthermore, by determining whether or not the inside of the cooling water channel 13 through which cooling water flows is filled with cooling water, the controller 35 is able to determine whether or not the inside of the reforming water channel 18 is filled with reforming water. It is therefore possible to suppress manufacturing costs compared to a configuration in which, for example, the cooling water channel 13 and the reforming water channel 18 are configured in such a way as to be channels of separate systems, and whether or not the respective channels are filled with cooling water or reforming water is detected separately. Furthermore, since tap water does not flow through either the cooling water channel 13 or the reforming water channel 18, it is possible to prevent the occurrence of scale. It is therefore not necessary to use expensive pipes to which it is difficult for scale to adhere when forming the cooling water channel 13 and the reforming water channel 18 and manufacturing costs can be suppressed.

It should be noted that the step in which the heater 30 is made to turn on in step S12, and the step in which the water supply pump 19 is made to operate in step S13 may be reversed in terms of the order thereof, or may be carried out at the same time.

Incidentally, the profile of the temperature detected by the first temperature detector 31 depicted in FIG. 5 is a temperature profile in which the temperature of the inner side of a pipe is detected by the first temperature detector 31 in a configuration in which a stainless steel such as SUS304, SUS316L, or SUS430 is used as the material of the pipe of the cooling water channel 13 and the heater 30 is provided in such a way as to surround the outer periphery of the pipe of the cooling water channel 13, for example. However, the material of the pipe of the cooling water channel 13 is not restricted to these stainless steels, and may be configured of a heat-resistant resin, for example. Furthermore, the heater 30 is not restricted to a configuration in which the heater 30 is provided in such a way as to surround the outer periphery of the pipe of the cooling water channel 13, and may have a configuration in which the heater 30 is provided inside the cooling water channel 13, for example. Furthermore, the temperature detected by the first temperature detector 31 is not restricted to being the temperature of the inner side of the pipe of the cooling water channel 13 and may be the temperature of the inside of the cooling water channel 13. The temperature profile depicted in FIG. 5 differs according to differences in the site where detection is performed by the first temperature detector 31, the type of the heater 30 provided in the cooling water channel 13, the pipe material of the cooling water channel 13, and the like; however, by setting t1, $\Delta T_a$, and $\Delta T_b$ in an appropriate manner according to each of those conditions, it is possible to appropriately determine whether or not there is cooling water inside the cooling water channel 13 and whether or not there is reforming water inside the reforming water channel 18.

Modified Example 1 of Embodiment 1

Figure 7:
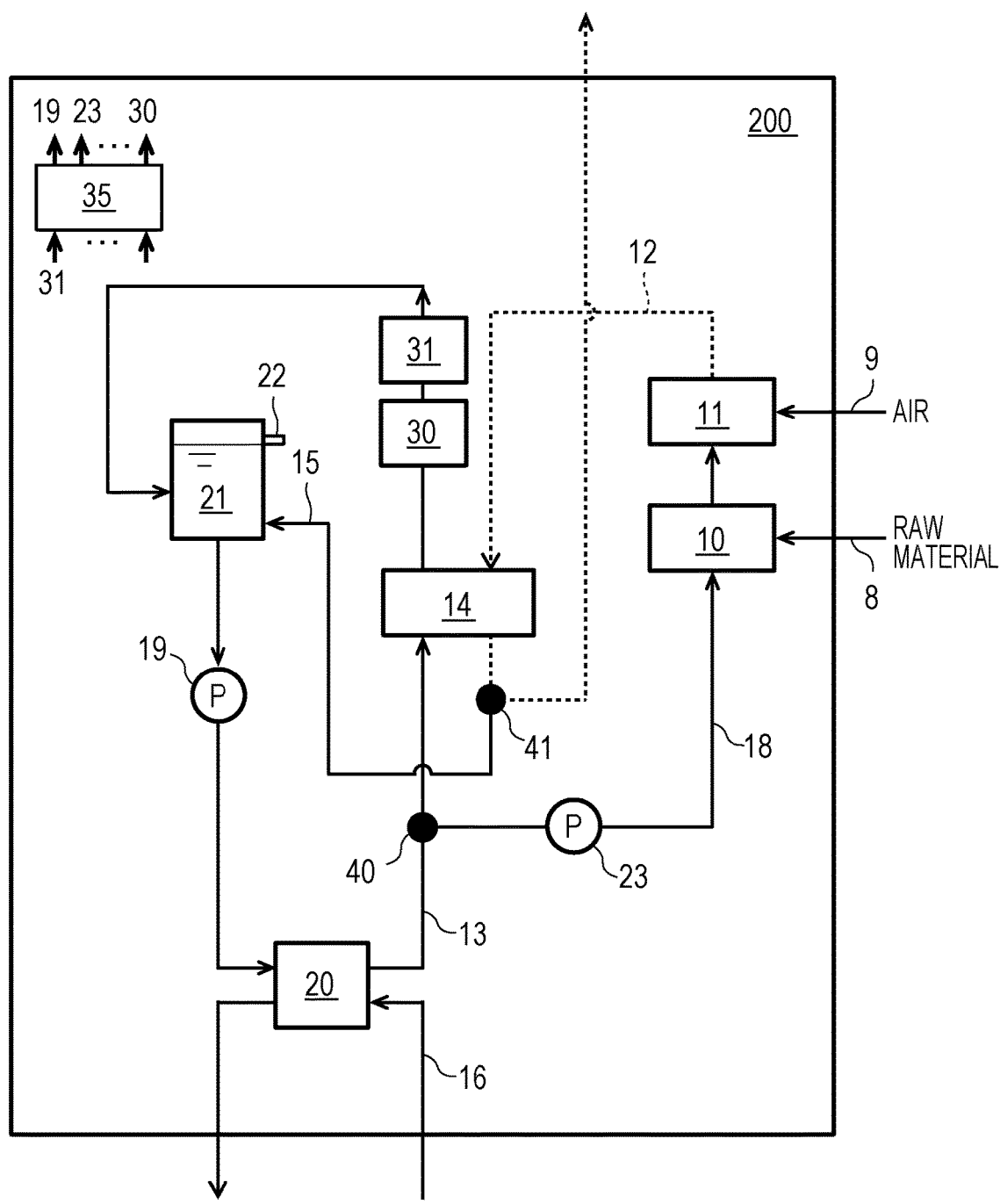
FIG. 7 is a drawing depicting an example of a schematic configuration of a hydrogen generation system according to modified example 1 of embodiment 1 of the present disclosure.

Next, a hydrogen generation system 200 according to modified example 1 of embodiment 1 will be described with reference to FIG. 7. FIG. 7 is a drawing depicting an example of a schematic configuration of the hydrogen generation system 200 according to modified example 1 of embodiment 1 of the present disclosure.

The configuration of the hydrogen generation system 200 according to modified example 1 of embodiment 1 is different in terms of the following points compared to the configuration of the hydrogen generation system 100 according to embodiment 1. In other words, the hydrogen generation system 100 according to embodiment 1 had a configuration in which cooling water flowing through the cooling water channel 13 is discharged outside the system, and had a configuration in which ion exchange water is supplied as cooling water to the water tank 21 from outside. In contrast, the hydrogen generation system 200 according to modified example 1 of embodiment 1 is different in that the cooling water channel 13 is a circulation channel which returns to the water tank 21 rather than going outside the system. That is, the hydrogen generation system 200 does not have a configuration in which ion exchange water is supplied as cooling water to the water tank 21 from outside. Furthermore, the hydrogen generation system 200 according to modified example 1 of embodiment 1 is different from the hydrogen generation system 100 according to embodiment 1 also in that a heat dissipator 20 is additionally provided between the water supply pump 19 and the first branching part 40 in the cooling water channel 13. In other respects, the hydrogen generation system 200 according to modified example 1 of embodiment 1 has a similar configuration to that of the hydrogen generation system 100 according to embodiment 1, and therefore similar members are denoted by the same reference numbers and descriptions thereof are omitted.

In the case where the cooling water channel 13 is formed as a circulation channel, cooling water circulates by sequentially flowing through the water tank 21, the water supply pump 19, the heat dissipator 20, the first branching part 40, the condenser 14, the heater 30, and the first temperature detector 31. It should be noted that the positional relationship between the heater 30 and the first temperature detector 31, as depicted in FIG. 7, may have a configuration in which the first temperature detector 31 is provided at a stage subsequent to the heater 30, or may have a configuration in which the first temperature detector 31 is provided at a stage prior to the heater 30 as long as it is a position where it is possible to detect temperature changes of the cooling water channel 13 which accompany the heating performed by the heater 30.

Furthermore, as depicted in FIG. 7, in the cooling water channel 13, an end part which is upstream in the flow direction of the cooling water is connected to a bottom part of the water tank 21, and a downstream end part is connected at a location that is lower than the overflow channel 22 provided in the water tank 21 and higher than the section where the condensed water channel 15 is connected. In this way, a configuration is adopted in which the upstream end part and the downstream end part of the cooling water channel 13 are both connected to the water tank 21.

The heat dissipator 20 is a device which causes the temperature of the cooling water flowing through the cooling water channel 13 to lower before reaching at least the condenser 14. In other words, in the hydrogen generation system 200, because the cooling water channel 13 is formed in such a way as to constitute a circulation channel, it is necessary for the temperature of the cooling water, which has become hot water due to heat exchange with exhaust gas in the condenser 14, to be lowered before reaching at least the condenser 14. Therefore, it is sufficient as long as the heat dissipator 20 is a device capable of dissipating heat from and cooling the cooling water flowing through the cooling water channel 13, and a possible example is an air-cooled radiator, a water-cooled plate-type heat exchanger, or the like. In the case the heat dissipator 20 is a radiator, air can be used as a heating medium that flows through a heating medium channel 16. Furthermore, in the case where the heat dissipator 20 is a water-cooled plate-type heat exchanger, water can be used as the heating medium flowing through the heating medium channel 16.

According to these configurations, the hydrogen generation system 200 according to modified example 1 of embodiment 1 becomes a self-contained system in which it is not necessary for cooling water (ion exchange water) to be supplied or additionally supplied from outside, and cooling water flowing through the cooling water channel 13 and condensed water generated by the condenser 14 can be used as cooling water and reforming water.

Furthermore, in the hydrogen generation system 200 according to modified example 1 of embodiment 1, it is also possible to determine whether or not there is cooling water inside the cooling water channel 13 in the activation operation mode, in a manner similar to the abnormality detection processing in the hydrogen generation system 100 according to embodiment 1 depicted in FIG. 6. Therefore, a description of the abnormality detection processing in the hydrogen generation system 200 according to modified example 1 of embodiment 1 is omitted.

(Arrangement of First Temperature Detector and Heater)

Figure 8:
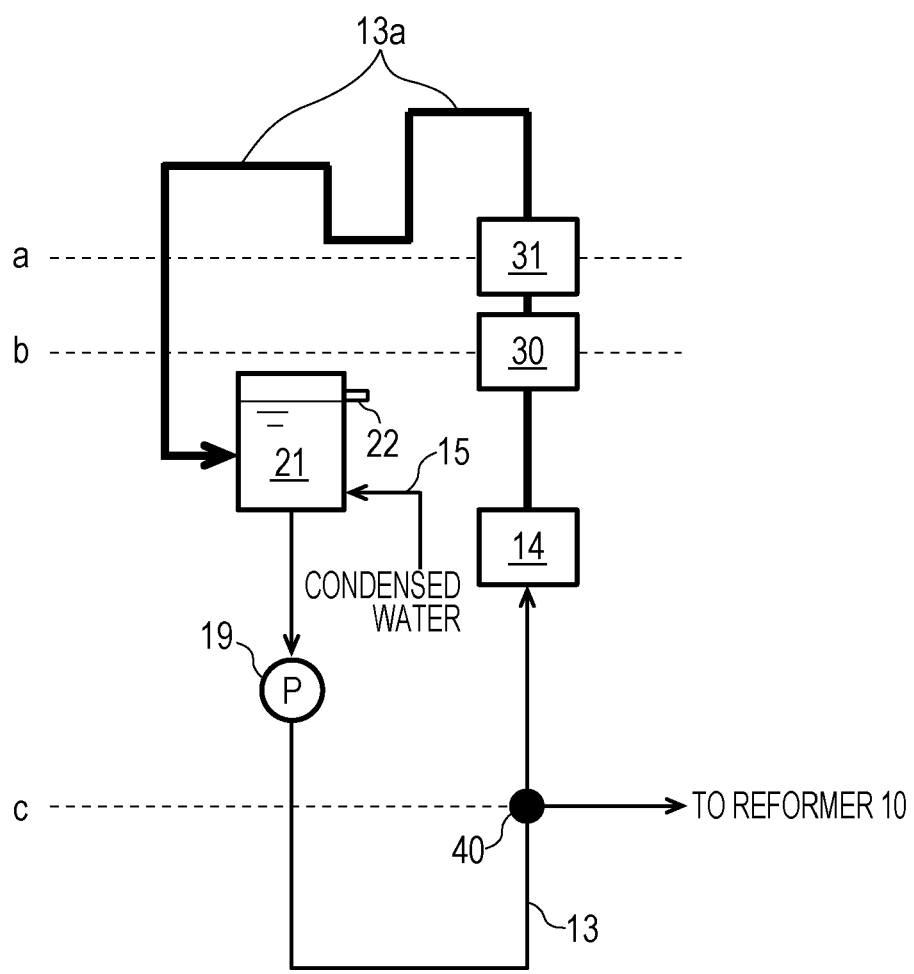
FIG. 8 is a drawing schematically representing an example of the arrangement relationship between a water tank, a water supply pump, a first branching part, a condenser, the heater, and the first temperature detector in the cooling water channel.

Next, the locations where the first temperature detector 31 and the heater 30 in the cooling water channel 13 are provided will be described. In the hydrogen generation system 100 according to embodiment 1 of the present disclosure having the aforementioned configuration and the hydrogen generation system 200 according to modified example 1 thereof, the water tank 21, the water supply pump 19, the first branching part 40, the condenser 14, the heater 30, and the first temperature detector 31 are arranged sequentially, from the upstream side in the flow direction of the cooling water, in the cooling water channel 13. That is, the heater 30 and the first temperature detector 31 are provided in locations which are higher than the first branching part 40, and locations which are a stage subsequent to the condenser 14 in the cooling water channel 13. In particular, in the case where the cooling water channel 13 is a circulation channel as in the hydrogen generation system 200 according to modified example 1 of embodiment 1, as depicted in FIG. 8, the locations (a and b in FIG. 8) of the heater 30 and the first temperature detector 31 in the height direction are locations which are higher than the location (c in FIG. 8) of the first branching part 40 in the height direction, and can be provided in any position between the condenser 14 and the water tank 21 in the cooling water channel 13. FIG. 8 is a drawing schematically representing an example of the arrangement relationship between the water tank 21, the water supply pump 19, the first branching part 40, the condenser 14, the heater 30, and the first temperature detector 31 in the cooling water channel 13.

In this way, the first temperature detector 31 and the heater 30 are arranged further downstream than the condenser 14 in the cooling water channel 13, namely further downstream than the first branching part 40, and in locations which are physically high. Therefore, when the controller 35 determines that the inside of the cooling water channel 13 is filled with cooling water on the basis of the temperature of the cooling water channel 13 detected by the first temperature detector 31, it is possible to guarantee that there is always reforming water inside the reforming water channel 18, and it is consequently possible to accurately determine whether or not there is reforming water. Therefore, in the hydrogen generation system 100 and the hydrogen generation system 200, it is possible to prevent a decline in performance of the reform catalyst of the reformer 10 caused by a shortage in the supply of reforming water.

Furthermore, as depicted in FIG. 8, in the hydrogen generation system 200, there may be one or more bent parts, between the condenser 14 and the water tank 21, in the cooling water channel 13 due to the installation space. In cases such as this, upwardly protruding sections 13a may be formed between the condenser 14 and the water tank 21 in the cooling water channel 13. There is a possibility that gas bubbles included in the cooling water may accumulate in these sections 13a, and if the first temperature detector 31 is provided in a portion in which these gas bubbles have accumulated, it may not be possible to accurately determine whether or not the inside of the cooling water channel 13 is filled with cooling water on the basis of a detection result of the first temperature detector 31. Thus, desirably, the heater 30 and the first temperature detector 31 may be provided in locations other than the sections 13a, between the condenser 14 and the water tank 21.

Embodiment 2

Figure 9:
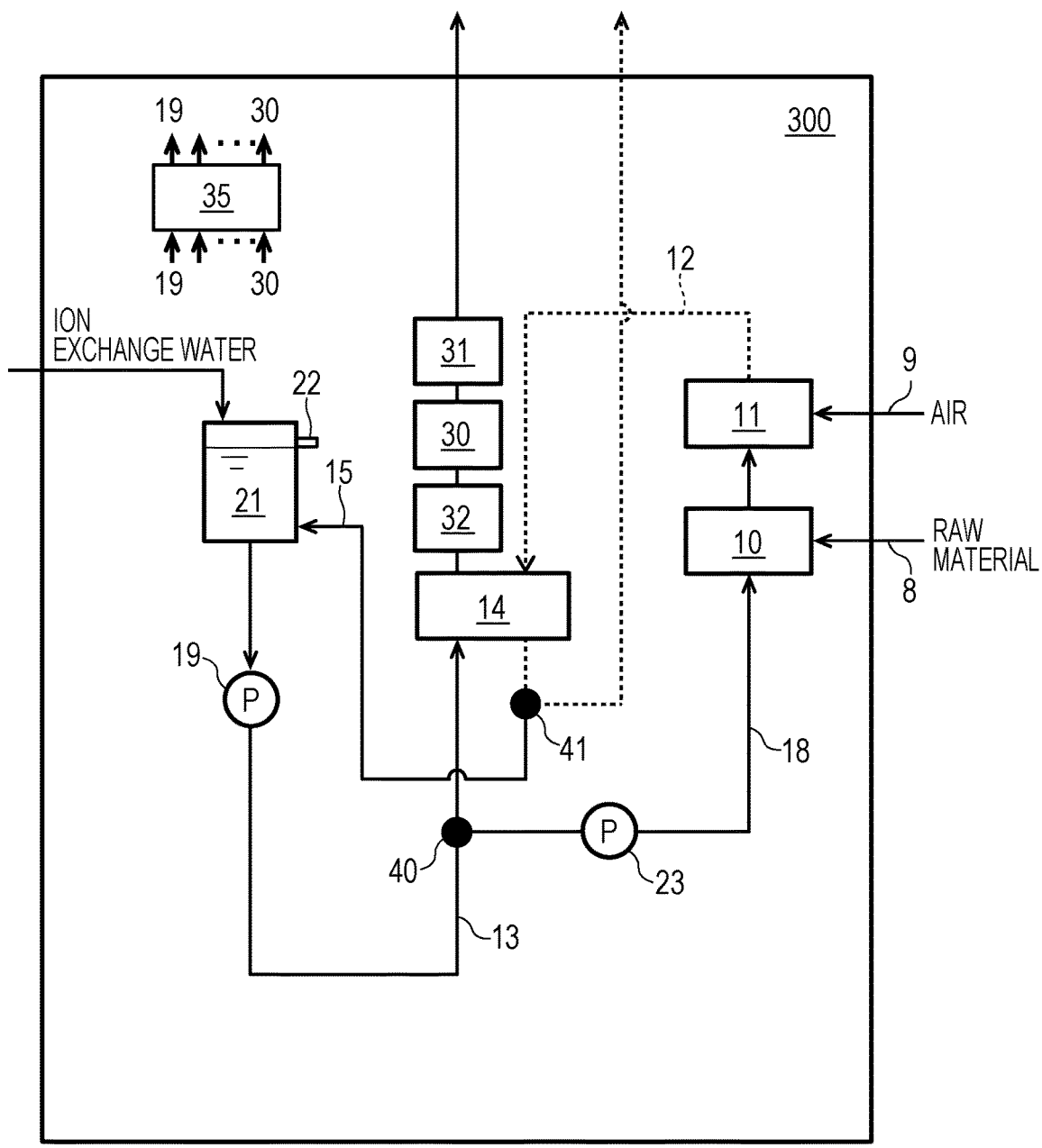
FIG. 9 is a drawing depicting an example of a schematic configuration of a hydrogen generation system according to embodiment 2 of the present disclosure.

Next, a hydrogen generation system 300 according to embodiment 2 will be described with reference to FIG. 9. FIG. 9 is a drawing depicting an example of a schematic configuration of the hydrogen generation system 300 according to embodiment 2 of the present disclosure. As depicted in FIG. 9, the hydrogen generation system 300 according to embodiment 2 is different in being additionally provided, in the configuration of the hydrogen generation system 100 according to embodiment 1, with a second temperature detector 32 which detects the temperature of the cooling water, at a location that is on the cooling water channel 13, a stage subsequent to the condenser 14, and a stage prior to the heater 30 and the first temperature detector 31. In other respects, the hydrogen generation system 300 according to embodiment 2 has a similar configuration to that of the hydrogen generation system 100 according to embodiment 1, and therefore similar members are denoted by the same reference numbers and descriptions thereof are omitted.

The second temperature detector 32 is able to detect the temperature of cooling water after the heat exchange with the exhaust gas carried out in the condenser 14. It is sufficient as long as the second temperature detector 32 has a configuration capable of detecting the temperature inside the cooling water channel 13 in a manner similar to the first temperature detector 31, and, for example, the second temperature detector 32 may be a thermistor or the like.

That is, the hydrogen generation system 100 according to the aforementioned embodiment 1 was a configuration in which whether or not there is cooling water inside the cooling water channel 13, in other words, whether or not there is reforming water inside the reforming water channel 18, is determined according to whether or not the temperature ($T_{x-1}$) detected by the first temperature detector 31 after the predetermined time (t1) has elapsed is equal to or less than the temperature $T_b$. However, the hydrogen generation system 300 according to embodiment 2 has a configuration in which whether or not there is cooling water inside the cooling water channel 13, in other words, whether or not there is reforming water inside the reforming water channel 18, is determined from the difference between temperatures detected before and after the heater 30.

Figure 10:
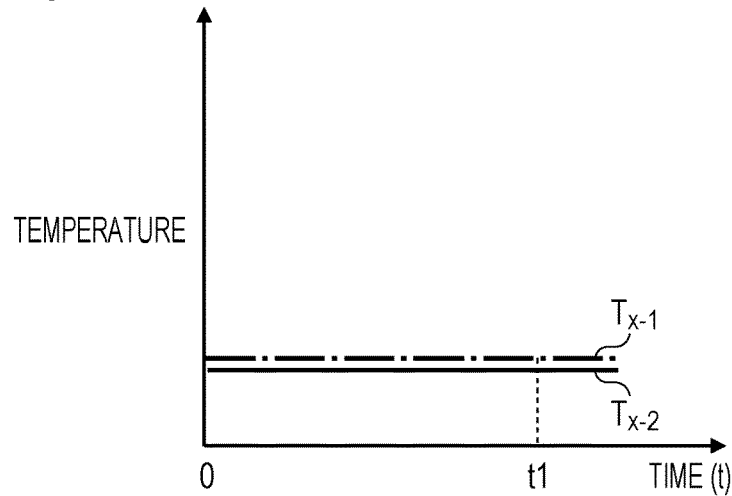
FIG. 10 is a graph depicting an example of detection results of a first temperature detector and a second temperature detector obtained when a heater has not operated in the hydrogen generation system depicted in FIG. 9.

That is, in the case where the heater 30 is not operating due to an abnormality, a state is entered in which there is substantially no difference between the temperature detected by the second temperature detector 32 provided at a stage prior to the heater 30 and the temperature detected by the first temperature detector 31 provided at a stage subsequent to the heater 30, as depicted in FIG. 10. FIG. 10 is a graph depicting an example of detection results of the first temperature detector 31 and the second temperature detector 32 obtained when the heater 30 has not operated in the hydrogen generation system 300 depicted in FIG. 9.

Figure 11:
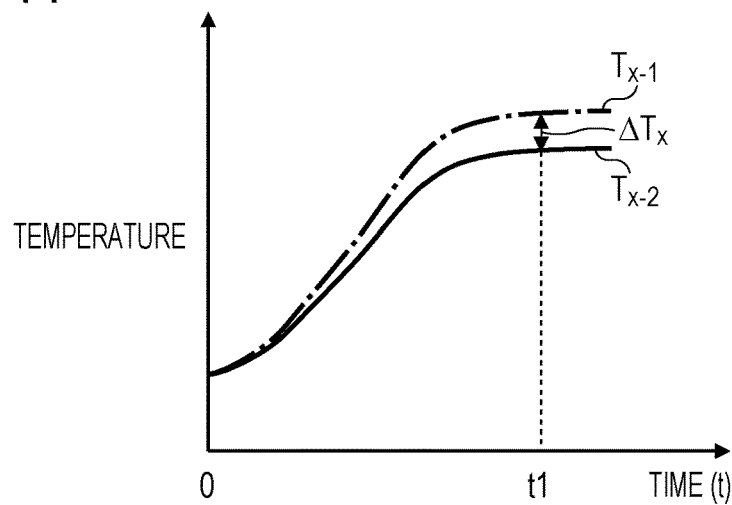
FIG. 11 is a graph depicting an example of detection results of the first temperature detector and the second temperature detector obtained when the heater is operating normally and there is no cooling water inside a cooling water channel in the hydrogen generation system depicted in FIG. 9.
Figure 12:
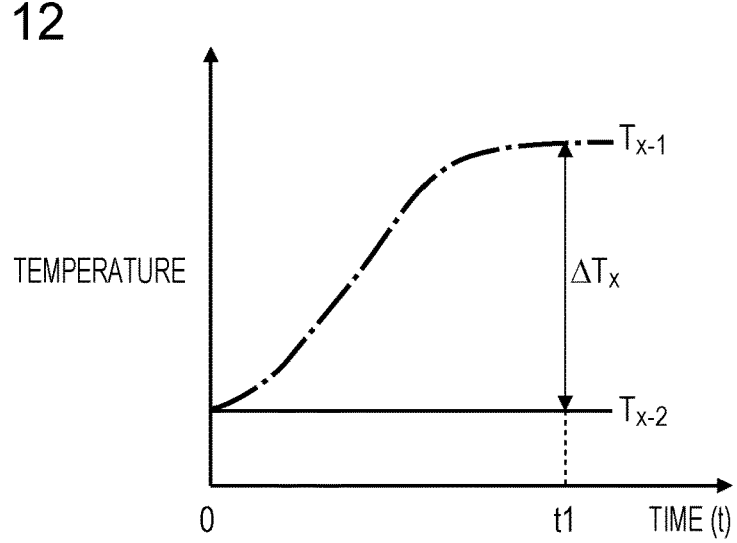
FIG. 12 is a graph depicting an example of detection results of the first temperature detector and the second temperature detector obtained when the heater is operating normally and there is cooling water inside the cooling water channel in the hydrogen generation system depicted in FIG. 9.
Figure 13:
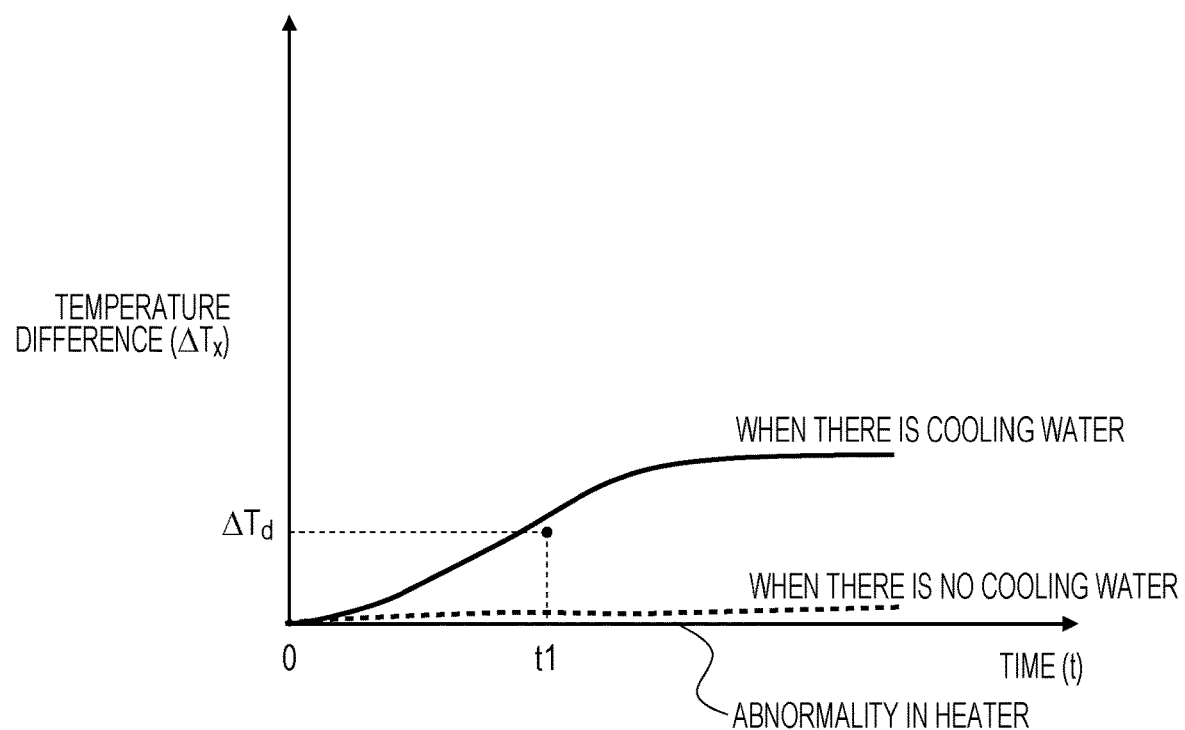
FIG. 13 is a graph depicting the relationship between a temperature difference of the first temperature detector and the second temperature detector when there is cooling water, and a temperature difference of the first temperature detector and the second temperature detector when there is no cooling water, in the hydrogen generation system depicted in FIG. 9.

However, in the case where the heater 30 is operating normally, a difference occurs between the temperature detected by the first temperature detector 31 and the temperature detected by the second temperature detector 32, as depicted in FIGS. 11 and 12. Furthermore, this temperature difference becomes larger in the case where there is cooling water in the cooling water channel 13 compared to the case where there is no cooling water, as depicted in FIG. 12. FIG. 11 is a graph depicting an example of detection results of the first temperature detector 31 and the second temperature detector 32 obtained when the heater 30 is operating normally and there is no cooling water inside the cooling water channel 13 in the hydrogen generation system 300 depicted in FIG. 9. FIG. 12 is a graph depicting an example of detection results of the first temperature detector 31 and the second temperature detector 32 obtained when the heater 30 is operating normally and there is cooling water inside the cooling water channel 13 in the hydrogen generation system 300 depicted in FIG. 9. FIG. 13 is a graph depicting the relationship between a temperature difference of the first temperature detector 31 and the second temperature detector 32 when there is cooling water, and a temperature difference of the first temperature detector 31 and the second temperature detector 32 when there is no cooling water, in the hydrogen generation system 300 depicted in FIG. 9.

Thus, the hydrogen generation system 300 according to embodiment 2 is configured in such a way that whether or not there is cooling water in the cooling water channel 13 is determined using the magnitude of the difference between the temperature detected by the first temperature detector 31 and the temperature detected by the second temperature detector 32.

That is, when the controller 35 causes the heater 30 to turn on and the cooling water channel 13 is heated in the case where the inside of the cooling water channel 13 is filled with cooling water, the temperature detected in the first temperature detector 31 gradually increases whereas the temperature detected in the second temperature detector 32 hardly changes. However, when the controller 35 causes the heater 30 to turn on and the cooling water channel 13 is heated in the case where the inside of the cooling water channel 13 is not filled with cooling water, the temperature detected in the first temperature detector 31 and the temperature detected in the second temperature detector 32 rise in substantially the same manner. Therefore, the temperature difference becomes larger in the case where the inside of the cooling water channel 13 is filled with cooling water than in the case where the inside of the cooling water channel 13 is not filled with cooling water. Thus, a configuration is adopted in which the controller 35 is able to determine whether or not there is cooling water inside the cooling water channel 13 on the basis of the difference between the temperature detected by the first temperature detector 31 and the temperature detected by the second temperature detector 32.

It should be noted that, in the steady operation mode, the cooling water flowing through the cooling water channel 13 is heated by heat exchange with the exhaust gas in the condenser 14. Thus, the controller 35 is also able to detect whether or not the combustor 11 is operating normally, based on the temperature of the cooling water detected by the first temperature detector 31 and the second temperature detector 32.

Hereinafter, abnormality detection processing in the hydrogen generation system 300 according to embodiment 2 will be specifically described with reference to FIG. 14 in addition to the aforementioned FIGS. 11 to 13.

(Abnormality Detection Processing in Hydrogen Generation System According to Embodiment 2)

Figure 14:
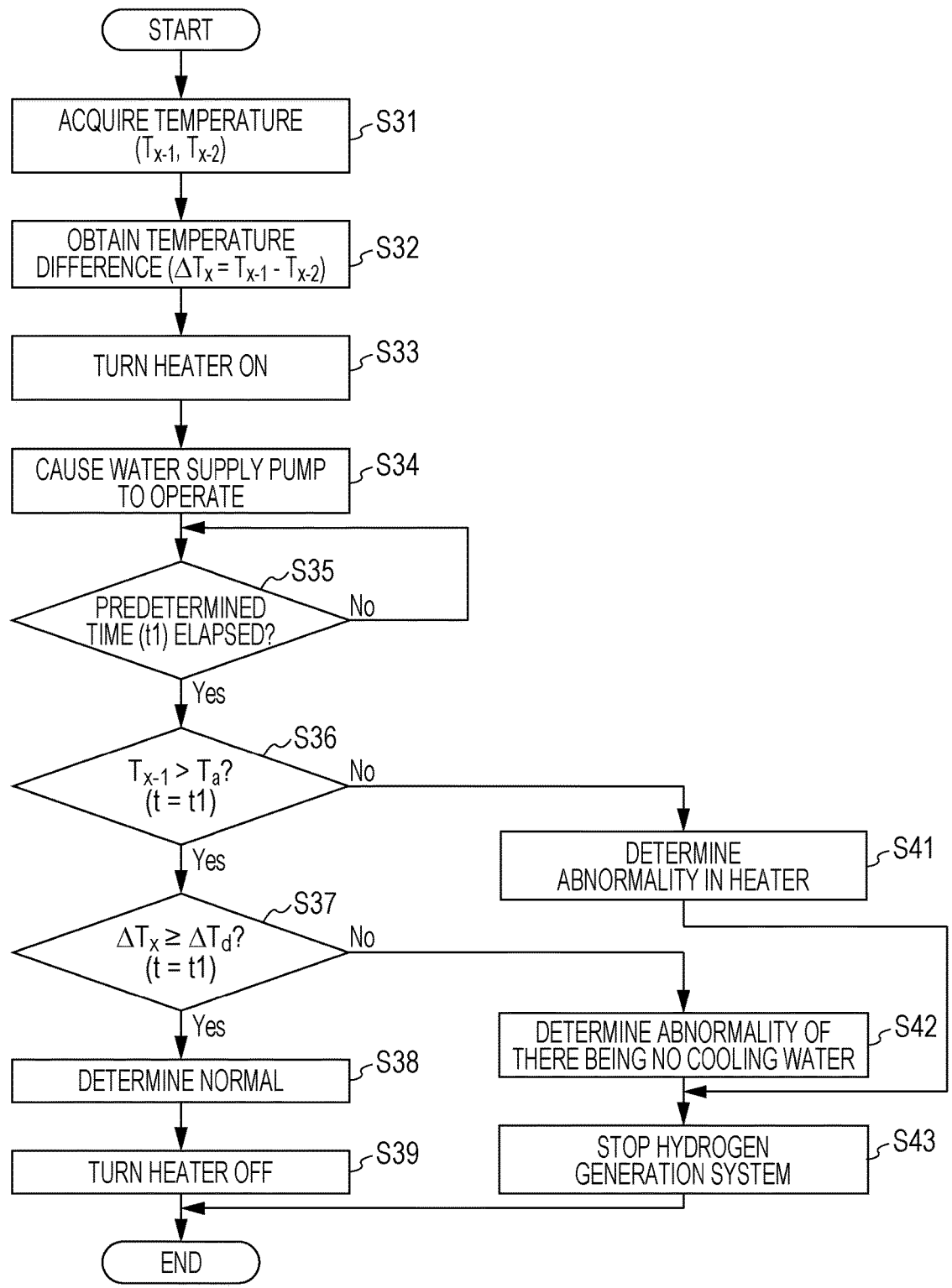
FIG. 14 is a flowchart depicting an example of abnormality detection processing in the hydrogen generation system depicted in FIG. 9.

FIG. 14 is a flowchart depicting an example of abnormality detection processing in the hydrogen generation system 300 depicted in FIG. 9. It should be noted that each processing step depicted in the flowchart of FIG. 14 is, for example, carried out by the controller 35 reading and executing a control program from a memory or the like when the activation operation mode is commenced. That is, when the operation mode of the hydrogen generation system 300 is switched from the stopped/standby mode to the activation operation mode, the controller 35 executes each step as depicted in the flowchart of FIG. 14.

First, the controller 35 acquires a temperature $T_{x-1}$ of the cooling water channel 13 detected by the first temperature detector 31 and a temperature $T_{x-2}$ of the cooling water channel 13 detected by the second temperature detector 32 (step S31). The controller 35 then obtains the temperature difference $\Delta T_x$ ($\Delta T_x = T_{x-1} - T_{x-2}$) between the temperature $T_{x-1}$ detected by the first temperature detector 31 and the temperature $T_{x-2}$ detected by the second temperature detector 32 (step S32).

It should be noted that the subsequent steps S33 to S36, S41, and S43 are similar to the steps S12 to S15, S21, and S23 depicted in FIG. 6 and therefore descriptions thereof are omitted.

In step S36, it is determined whether or not the temperature $T_{x-1}$ detected by the first temperature detector 31 is higher than the temperature $T_a$, and in the case where it is determined that the temperature $T_{x-1}$ is higher than the temperature $T_a$ (in the case of yes in step S36), the controller 35 transitions to step S37.

In step S37, the controller 35 determines whether or not the temperature difference $\Delta T_x$ between the temperature $T_{x-1}$ detected by the first temperature detector 31 and the temperature $T_{x-2}$ detected by the second temperature detector 32 is equal to or greater than a predetermined temperature difference ($\Delta T_d$) which is determined in advance. Here, $\Delta T_d$ is a value indicating the difference between the temperature detected by the first temperature detector 31 and the temperature detected by the second temperature detector 32 which occurs at least when the cooling water path 13 is heated by the heater 30 during the predetermined time (t1) in the case where cooling water has filled the inside of the cooling water channel 13, or is a value which is slightly lower than this temperature difference, as depicted in FIG. 13. $\Delta T_d$ can be obtained in advance from an actual device evaluation, simulation, or the like, and can be stored in a memory or the like which is not depicted.

Here, in the case where it is determined that the temperature difference $\Delta T_x$ is lower than the predetermined temperature difference ($\Delta T_d$) (in the case of no in step S37), the controller 35 determines that the abnormality of the cooling water not having filled the cooling water channel 13 has occurred (step S42), and performs control in such a way that the operation of the hydrogen generation system in the activation operation mode is stopped (step S43).

However, in the case where it is determined that the temperature difference $\Delta T_x$ is equal to or greater than the predetermined temperature difference ($\Delta T_d$) (in the case of yes in step S37), the controller 35 determines that the cooling water has filled the cooling water channel 13 and that operation is normal (step S38), and transitions to step S39. In step S39, the controller 35 causes the passage of current to the heater 30 to be stopped (turned off).

Thereafter, the controller 35 causes the raw material to be supplied to the reformer 10, and causes the reforming water supply pump 23 to operate and reforming water to be supplied. Furthermore, the controller 35 causes air to be supplied to the combustor 11, and causes the combustor 11 to ignite. Then, if the temperature of the reformer 10 becomes equal to or greater than a predetermined temperature using the heat of the exhaust gas generated by the combustion in the combustor 11, the activation operation mode is ended and a transition is made to the steady operation mode.

The hydrogen generation system 300 according to embodiment 2 as mentioned above has a configuration in which a portion of the cooling water is supplied to the reformer 10 through the reforming water channel 18 which branches from the cooling water channel 13. In a configuration such as this, the second temperature detector 32, the heater 30, and the first temperature detector 31 are installed at a stage subsequent to the first branching part 40, and it is possible to confirm whether or not there is cooling water in the cooling water channel 13, in other words, whether or not there is reforming water in the reforming water channel 18, based on the temperature difference $\Delta T_x$ between the temperature detected by the first temperature detector 31 and the temperature detected by the second temperature detector 32. In this way, with the hydrogen generation system 300 according to embodiment 2, it is possible to determine, from the state of the cooling water channel 13, a shortage in the supply of reforming water to the reformer 10 in the activation operation mode.

Furthermore, by determining whether or not the inside of the cooling water channel 13 through which cooling water flows is filled with cooling water, the controller 35 is able to determine whether or not the inside of the reforming water channel 18 is filled with reforming water. It is therefore possible to suppress manufacturing costs compared to a configuration in which, for example, the cooling water channel 13 and the reforming water channel 18 are configured in such a way as to be channels of separate systems, and whether or not the respective channels are filled with cooling water or reforming water is detected separately. Furthermore, since tap water does not flow through either the cooling water channel 13 or the reforming water channel 18, it is possible to prevent the occurrence of scale. It is therefore not necessary to use expensive pipes to which it is difficult for scale to adhere when forming the cooling water channel 13 and the reforming water channel 18 and manufacturing costs can be suppressed.

Modified Example 1 of Embodiment 2

Figure 15:
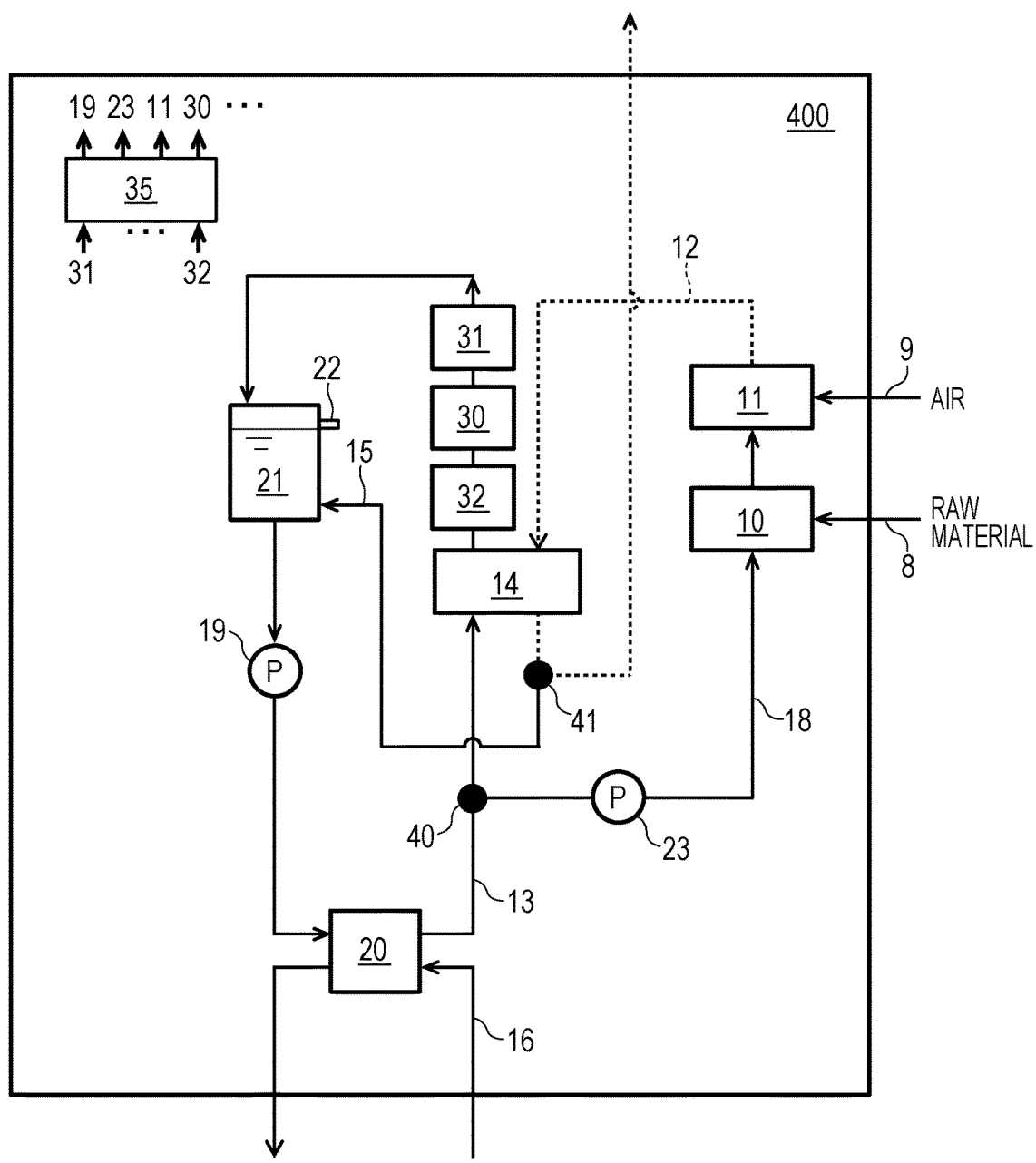
FIG. 15 is a drawing depicting an example of a schematic configuration of a hydrogen generation system according to modified example 1 of embodiment 2 of the present disclosure.

Next, a hydrogen generation system 400 according to modified example 1 of embodiment 2 will be described with reference to FIG. 15. FIG. 15 is a drawing depicting an example of a schematic configuration of the hydrogen generation system 400 according to modified example 1 of embodiment 2 of the present disclosure.

The configuration of the hydrogen generation system 400 according to modified example 1 of embodiment 2 is different in terms of the following points compared to the configuration of the hydrogen generation system 300 according to embodiment 2. In other words, the hydrogen generation system 300 according to embodiment 2 had a configuration in which cooling water flowing through the cooling water channel 13 is discharged outside the system, and had a configuration in which ion exchange water is supplied as cooling water to the water tank 21 from outside. In contrast, the hydrogen generation system 400 according to modified example 1 of embodiment 2 is different in that the cooling water channel 13 is a circulation channel which returns to the water tank 21 rather than going outside the system. That is, the hydrogen generation system 400 does not have a configuration in which ion exchange water is supplied as cooling water to the water tank 21 from outside. Furthermore, the hydrogen generation system 400 according to modified example 1 of embodiment 2 is different from the hydrogen generation system 300 according to embodiment 2 also in that the heat dissipator 20 is additionally provided between the water supply pump 19 and the first branching part 40 in the cooling water channel 13. In other respects, the hydrogen generation system 400 according to modified example 1 of embodiment 2 has a similar configuration to that of the hydrogen generation system 300 according to embodiment 2, and therefore similar members are denoted by the same reference numbers and descriptions thereof are omitted.

Furthermore, it can be said that the hydrogen generation system 400 according to modified example 1 of embodiment 2 has a configuration additionally provided with the second temperature detector 32 between the condenser 14 and the heater 30, in addition to the configuration of the hydrogen generation system 200 according to modified example 1 of embodiment 1. Therefore, the cooling water channel 13 formed as a circulation channel and the heat dissipator 20 are similar to those of the hydrogen generation system 200 according to modified example 1 of embodiment 1, and therefore detailed descriptions thereof are omitted.

Furthermore, in the hydrogen generation system 400 according to modified example 1 of embodiment 2, it is also possible to determine whether or not there is cooling water inside the cooling water channel 13 in the activation operation mode, in a manner similar to the abnormality detection processing in the hydrogen generation system 300 according to embodiment 2 depicted in FIG. 14. Therefore, a description of the abnormality detection processing in the hydrogen generation system 400 according to modified example 1 of embodiment 2 is omitted.

Embodiment 3

Figure 16:
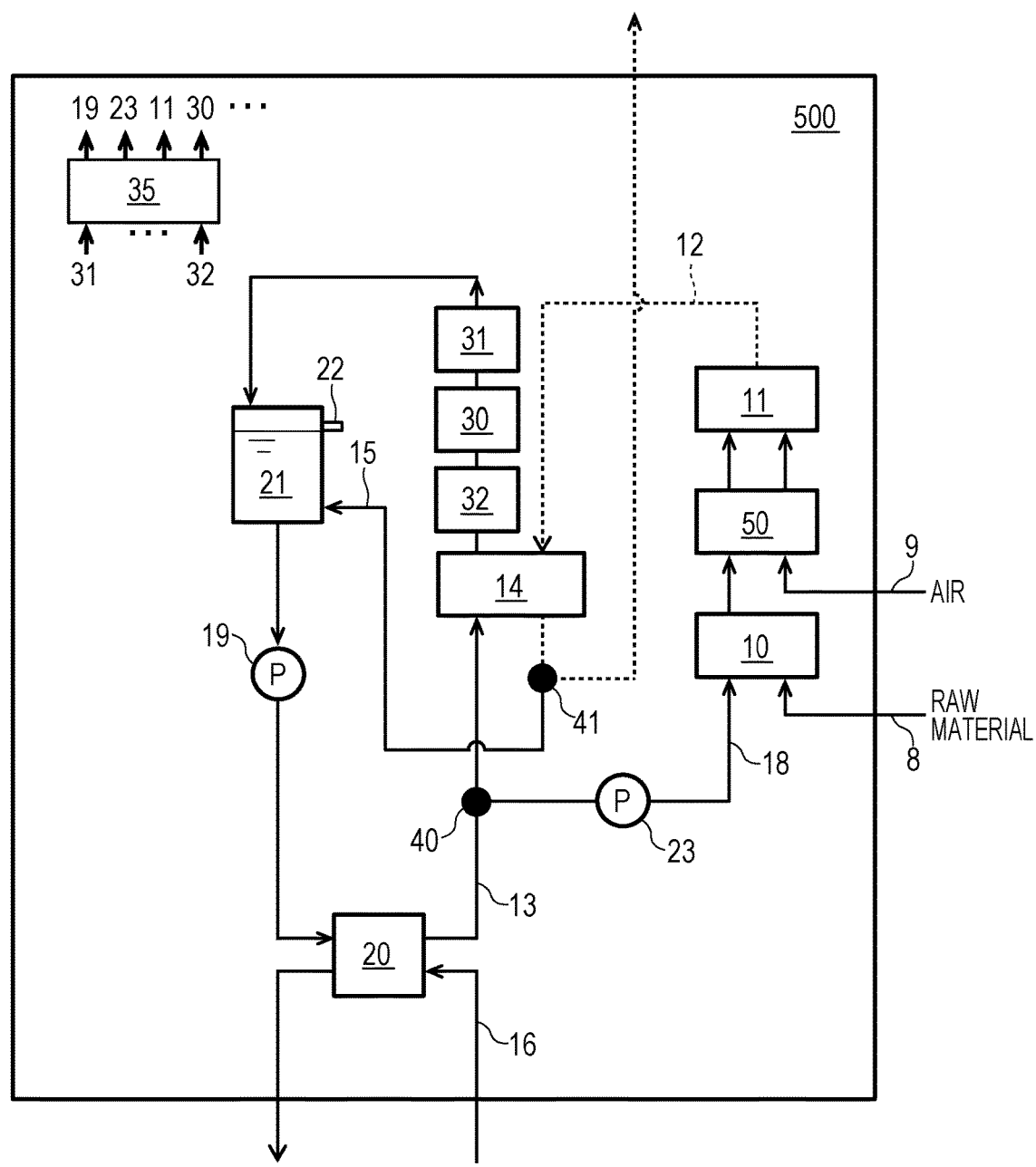
FIG. 16 is a drawing depicting an example of a schematic configuration of a fuel cell system according to embodiment 3 of the present disclosure.

Next, as embodiment 3, a fuel cell system provided with the aforementioned hydrogen generation system 400 will be described with reference to FIG. 16 as an example. A fuel cell system 500 according to embodiment 3 has a configuration which is additionally provided with a fuel cell 50 in addition to the aforementioned hydrogen generation system 400. FIG. 16 is a drawing depicting an example of a schematic configuration of the fuel cell system 500 according to embodiment 3 of the present disclosure.

As depicted in FIG. 16, the fuel cell system 500 according to embodiment 3 is a system which generates electricity using a raw material supplied from outside and a hydrogen-containing gas generated by the reformer 10. The fuel cell system 500 has a configuration which is provided with the raw material supply channel 8, the air supply channel 9, the reformer 10, the combustor 11, the exhaust gas channel 12, the cooling water channel 13, the condenser 14, the condensed water channel 15, the heating medium channel 16, the reforming water channel 18, the water supply pump 19, the heat dissipator 20, the water tank 21, the reforming water supply pump 23, the heater 30, the first temperature detector 31, the second temperature detector 32, the controller 35, and the fuel cell 50. It should be noted that the water tank 21 may not be provided with the overflow channel 22.

In other words, in the fuel cell system 500 according to embodiment 3, the fuel cell 50 is additionally provided in the configuration of the hydrogen generation system 400 depicted in FIG. 15, and the supply destination of air supplied through the air supply channel 9 is the fuel cell 50 rather than the combustor 11. In other respects, the fuel cell system 500 has a similar configuration to that of the hydrogen generation system 400. Therefore, similar members are denoted by similar reference numbers, and descriptions thereof are omitted. In embodiment 3, a configuration is adopted in which the fuel cell 50 is additionally provided in the configuration of the hydrogen generation system 400; however, it should be noted that there is no restriction thereto. For example, a configuration may be adopted in which the fuel cell 50 is additionally provided in the configuration of the hydrogen generation system 100, the hydrogen generation system 200, or the hydrogen generation system 300.

The fuel cell 50 generates electricity using the hydrogen-containing gas generated by the reformer 10 and the air (oxygen-containing gas) supplied through the air supply channel 9. For example, the fuel cell 50 is provided with a single cell in which an electrolyte is interposed between an anode electrode and a cathode electrode to generate electricity due to the hydrogen-containing gas from the reformer 10 being supplied to the anode side and the air (oxygen-containing gas) being supplied to the cathode side. It should be noted that, in the fuel cell 50, a stack is formed in which a plurality of such single cells are electrically linked in series and a voltage of several volts to several hundred volts is generated. Furthermore, the fuel cell 50 may be a configuration which is provided with a manifold (not depicted) that distributes and supplies the air and hydrogen-containing gas to each single cell, and a current collecting unit (not depicted).

It should be noted that an anode off-gas including the hydrogen-containing gas which has not been used in the generation of electricity by the fuel cell 50 and a cathode off-gas including the air (oxidant gas) which has not been used in the generation of electricity are supplied to the combustor 11, and the anode off-gas and the cathode off-gas are combusted. Therefore, it can be said that the hydrogen-containing gas generated by the reformer 10 and the air supplied from outside are supplied via the fuel cell 50 to the combustor 11. Furthermore, in the case where the flow rate of the air supplied to the combustor 11 is insufficient, a configuration may be adopted in which an air supply channel is additionally provided and air is supplied to the combustor 11.

The fuel cell 50 is classified as a solid polymer fuel cell, a solid oxide fuel cell, a molten carbonate fuel cell, a phosphoric acid fuel cell, an alkali fuel cell, or the like according to the type of electrolyte in the single cell, and the fuel cell 50 may be any of these types.

For example, in the case where the fuel cell 50 is a solid oxide fuel cell, a solid electrolyte of yttria-stabilized zirconia (YSZ), which is zirconia ($ZrO_2$) to which an yttrium (Y) oxide ($Y_2O_3$) has been added, or zirconia which has been doped with ytterbium (Yb) or scandium (Sc) is used for the electrolyte, for example. In a single cell of the fuel cell 50 in which YSZ is used, an electricity generation reaction is carried out at a temperature range of approximately 500° C. to 1000° C., for example, although this is dependent on the thickness of the electrolyte. A mixture of nickel (Ni) and YSZ, a mixture in which gadolinium (Gd) has been added to an oxide ($CeO_2$) of nickel and cerium (Ce), or the like is used as the material of the anode, for example. Meanwhile, an oxide containing lanthanum, strontium, and manganese, an oxide containing lanthanum, strontium, cobalt, and iron, or the like is used as the material of the cathode, for example.

It should be noted that, in the fuel cell system 500, there are cases where the reformer 10 and the fuel cell 50 are treated as a single unit and are referred to as a fuel cell module. Furthermore, the structure of the single cells making up the fuel cell 50 may be any of a so-called planar type, cylindrical type, cylindrical planar type, or the like.

Furthermore, in the fuel cell system 500, the controller 35 may carry out processing steps similar to those of the abnormality detection processing depicted in FIG. 14. Alternatively, in the case where the fuel cell system 500 has a configuration which is additionally provided with the fuel cell 50 in the hydrogen generation system 100 according to embodiment 1 or the hydrogen generation system 200 according to modified example 1 of embodiment 1, the controller 35 may carry out processing steps similar to those of the abnormality detection processing depicted in FIG. 6. Furthermore, the fuel cell system 500 may have a configuration as a cogeneration system in which heat of the exhaust gas is recovered in the cooling water by the condenser 14 and the cooling water heated by the aforementioned heat is used as supplied hot water.

The present disclosure can be broadly applied in hydrogen generation systems in which moisture included in an exhaust gas is used to cool reforming water and the exhaust gas.

What is claimed is:

1. A hydrogen generation system comprising:
    a reformer which generates a hydrogen-containing gas using a raw material and reforming water;
    a combustor which combusts the hydrogen-containing gas generated by the reformer and air to generate an exhaust gas;
    an exhaust gas channel through which the exhaust gas is made to flow;
    a cooling water channel through which cooling water is made to flow in order to cool the exhaust gas;
    a condenser which causes moisture within the exhaust gas to be condensed by heat exchange between the exhaust gas and the cooling water to generate condensed water;
    a water tank which accumulates, as the cooling water, the condensed water generated in the condenser;
    a water supply pump which causes the cooling water accumulated inside the water tank to be supplied to the condenser;
    a reforming water channel which branches at a first branching part provided between the water supply pump and the condenser in the cooling water channel, and through which a portion of the cooling water is made to flow to the reformer as the reforming water;
    a heater which is provided further downstream than the first branching part in a flow direction of the cooling water in the cooling water channel, and which heats the cooling water channel;
    a first temperature detector which detects a temperature of the cooling water channel heated by the heater; and
    a controller,
    wherein, in an activation operation mode which is an operation mode from activation to steady operation of the hydrogen generation system, the controller is programmed to cause the heater to operate, and determine whether or not inside of the reforming water channel is filled with the reforming water, based on the temperature detected by the first temperature detector after the heater has operated.

2. The hydrogen generation system according to claim 1, wherein the controller is programmed to performs control in such a way that operation in the activation operation mode is made to stop when it is determined that the inside of the reforming water channel is not filled with the reforming water.

3. The hydrogen generation system according to claim 1, wherein, in the activation operation mode, the controller is programmed to perform control in such a way that the heater is made to operate before the combustor is made to ignite.

4. The hydrogen generation system according to claim 1, wherein the heater and the first temperature detector are provided in locations which are, in the flow direction of the cooling water in the cooling water channel, further downstream than the first branching part, and higher than the first branching part.

5. The hydrogen generation system according to claim 1, wherein the cooling water channel is a circulation channel in which the cooling water circulates flowing through the water tank, the water supply pump, the first branching part, the condenser, the heater, and the first temperature detector.

6. The hydrogen generation system according to claim 5, wherein the heater and the first temperature detector are provided in locations which are higher than the first branching part, and in a section between the condenser and the water tank in the cooling water channel.

7. The hydrogen generation system according to claim 1, wherein, in a steady operation mode which is an operation mode in which the hydrogen generation system is in steady operation, the first temperature detector detects a temperature of the cooling water which is discharged from the condenser, and
the controller is programmed to determines whether or not there is an abnormality hydrogen generation system in the steady operation mode, based on the temperature detected by the first temperature detector.

8. The hydrogen generation system according to claim 1, wherein the condenser, the heater, and the first temperature detector are arranged in this order, in the flow direction of the cooling water, in the cooling water channel.

9. The hydrogen generation system according to claim 8, wherein a second temperature detector which detects a temperature of the cooling water channel is provided at a location which is further downstream than the condenser and further upstream than the heater, in the flow direction of the cooling water, in the cooling water channel, and
the controller, based on the temperature detected by the second temperature detector in addition to the temperature detected by the first temperature detector, is programmed to obtains a difference between the temperature detected by the first temperature detector and the temperature detected by the second temperature detector, and is programmed to determines whether or not the inside of the reforming water channel is filled with the reforming water, according to this difference between the temperatures.

10. The hydrogen generation system according to claim 1, wherein a jig for arranging the heater in the cooling water channel is provided, and the first temperature detector is arranged in the cooling water channel as a single unit together with the heater by the jig.

11. The hydrogen generation system according to claim 1, wherein a jig for arranging the heater in the cooling water channel is provided, and the first temperature detector is arranged near the jig in the cooling water channel.

12. A fuel cell system comprising:
a reformer which generates a hydrogen-containing gas using a raw material and reforming water;
a fuel cell which generates electricity using the hydrogen-containing gas and air;
a combustor which combusts the hydrogen-containing gas and air which have not been used in generation of electricity by the fuel cell to generate an exhaust gas;
an exhaust gas channel through which the exhaust gas is made to flow;
a cooling water channel through which cooling water is made to flow in order to cool the exhaust gas;
a condenser which causes moisture within the exhaust gas to be condensed by heat exchange between the exhaust gas and the cooling water to generate condensed water;
a water tank which accumulates, as the cooling water, the condensed water generated in the condenser;
a water supply pump which causes the cooling water accumulated inside the water tank to be supplied to the condenser;
a reforming water channel which branches at a first branching part provided between the water supply pump and the condenser in the cooling water channel, and through which a portion of the cooling water is made to flow to the reformer as the reforming water;
a heater which is provided further downstream than the first branching part in a flow direction of the cooling water in the cooling water channel;
a first temperature detector which detects a temperature of the cooling water channel heated by the heater; and
a controller,
wherein, in an activation operation mode which is an operation mode from activation to stead operation of the fuel cell system, the controller is programmed to cause the heater to operate, and determines whether or not inside of the reforming water channel is filled with the reforming water, based on the temperature detected by the first temperature detector after the heater has operated.

13. The fuel cell system according to claim 12, wherein the fuel cell is a solid oxide fuel cell.

* * * * *